(12) United States Patent  (10) Patent No.: US 8,551,405 B2
Gabriel  (45) Date of Patent: *Oct. 8, 2013

(54) ELECTROPHORETIC INTERACTIVE SPECTRAL METHODS AND DEVICES FOR THE DETECTION AND/OR CHARACTERIZATION OF BIOLOGICAL PARTICLES

(75) Inventor: Don A. Gabriel, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 565 days.

This patent is subject to a terminal disclaimer.

(21) Appl. No.: 12/512,306

(22) Filed: Jul. 30, 2009

(65) Prior Publication Data

US 2010/0203499 A1  Aug. 12, 2010

Related U.S. Application Data

(62) Division of application No. 11/121,322, filed on May 3, 2005, now Pat. No. 7,771,660.

(60) Provisional application No. 60/568,128, filed on May 4, 2004.

(51) Int. Cl.
   *C12Q 1/04* (2006.01)
(52) U.S. Cl.
   USPC ....................................... 422/82.05
(58) Field of Classification Search
   None
   See application file for complete search history.

(56) References Cited

U.S. PATENT DOCUMENTS

| | | | |
|---|---|---|---|
| 3,870,612 A | 3/1975 | Flygare et al. | |
| 3,984,533 A | 10/1976 | Uzgiris | |
| 4,011,044 A | 3/1977 | Uzgiris | |
| 4,080,264 A | 3/1978 | Cohen et al. | |
| 4,097,153 A | 6/1978 | DeRimigis | |
| 4,102,990 A | 7/1978 | Uzgiris | |
| 4,385,113 A * | 5/1983 | Frosch et al. | 435/8 |
| 4,571,081 A | 2/1986 | Ford, Jr. | |
| 4,911,794 A | 3/1990 | Parce et al. | 205/778 |
| 5,108,568 A * | 4/1992 | Van Alstine | 204/450 |
| 5,202,264 A | 4/1993 | Benson et al. | |
| 5,578,460 A * | 11/1996 | Ebersole et al. | 435/29 |
| 5,581,349 A | 12/1996 | Halaka | |

(Continued)

FOREIGN PATENT DOCUMENTS

WO  WO 85/04486  10/1985

OTHER PUBLICATIONS

Li (1996) JBC 271" 11767-11771.*
Melton (2001) Blood Coag Fib 12:237-243.*

(Continued)

*Primary Examiner* — N. C. Yang
*Assistant Examiner* — Richard Moerschell
(74) *Attorney, Agent, or Firm* — Myers Bigel Sibley & Sajovec, PA

(57) ABSTRACT

Methods for identifying a biological particle in a sample medium include generating an Electrophoretic Quasi-elastic Light Scattering (EQELS) spectrum for the biological particle in the sample medium. The EQELS spectrum is compared to a reference database comprising a plurality of spectra, and each of the plurality of spectra correspond to an EQELS spectrum for one of a plurality of known biological particles. The biological particle in the sample medium is identified from the comparison.

36 Claims, 13 Drawing Sheets

(56) References Cited

U.S. PATENT DOCUMENTS

| | | | |
|---|---|---|---|
| 5,585,278 A | 12/1996 | Vunnam et al. | |
| 5,854,403 A | 12/1998 | Fischer et al. | |
| 5,945,293 A | 8/1999 | Siiman et al. | |
| 5,958,880 A * | 9/1999 | Frank et al. | 424/185.1 |
| 6,103,693 A | 8/2000 | Fischer et al. | |
| 6,291,423 B1 | 9/2001 | Bischoff et al. | |
| 6,361,965 B1 * | 3/2002 | Powell | 435/69.1 |
| 6,379,929 B1 | 4/2002 | Burns et al. | 435/91.2 |
| 6,586,193 B2 * | 7/2003 | Yguerabide et al. | 506/3 |
| 7,723,087 B2 * | 5/2010 | Pier et al. | 435/183 |
| 7,780,831 B2 * | 8/2010 | Gabriel | 204/452 |
| 2002/0025920 A1 | 2/2002 | Bischoff et al. | |
| 2002/0081632 A1 | 6/2002 | Wynn et al. | |
| 2003/0082516 A1 | 5/2003 | Straus et al. | |
| 2003/0124643 A1 | 7/2003 | Taintor | 435/40 |
| 2003/0129618 A1 | 7/2003 | Moronne et al. | |

OTHER PUBLICATIONS

Gabriel (1993) Blood Coag Fib 4:397-403.*
Smith (1976) PNAS 73:2388-2391.*
Li (1977) Biochemistry 36: 10760-10767.*
Li (1996) JBC 271:11767-11771.*
Knox et al., "A molecular mechanism for sensory adaptation based on ligand-induced receptor modification", 1986, Proc. Natl. Acad. Sci. USA, vol. 83, pp. 2345-2349.
Kogure et al., "Attachment of Vibrio alginolyticus to galss surfaces is depedent on swimming speed", 1998, J. Bacteriology, vol. 180, pp. 932-937.
Ahmad et al. "Comparative Interactions of Factor IX and Factor IXa with human Platelets" *J Biol Chem* 264(6): 3244-3251 (1989).
Ahmad et al. "Comparative Platelet Binding and Kinetic Studies with Normal and variant Factor IXa Molecules" *J Biol Chem* 265: 20907-20911 (1990).
Ahmad et al. "Platelet Receptor Occupancy with Factor IXa Promotes Factor X Activation" *J Biol Chem* 264: 20012-20016 (1989).
Ahmad et al. "The Role of the First Growth Factor Domain of Human Factor IXa in Binding to platelets and in Factor X Activation" *J Biol Chem* 267: 8570-8576 (1992).
Alonso, et al. High-risk (HPV16) human papillomavirus E7 oncoprotein is highly stable and extended, with conformational transitision that could explain its multiple cellular binding partners. *Biochemistry.* 41(33), 10510-8. (2002) [Abstract only].
Antoine et al., "ADAMTS13 Gene Defects in Two Brothers with Constitutional Thrombatic Thrombocytopenic Purpura and Normalization of von Willebrand Factor-Cleaving Protease Activity by Recombinant Human ADAMTS13," *British Journal of Haematology*, 120:821-854 (2003).
Ashida et al., "Successful Treatment of a Young Infant Who Developed High-Titer Inhibitors Against VWF-Cleaving Protease (ADAMTS-13): Important Discrimination from Upshaw-Schulman Syndrome," *American Journal of Hematology*, 71:318-322 (2002).
Barington et al., "A Very-High-Purity von Willebrand Factor Preparation Containing High-Molecular-Weight Multimers," http://BioMedNet.com/karger pp. 85-89 (1999).
Bauer et al. "Factor IX is Activated in Vivo by the Tissue Factor Mechanism" *Blood* 76: 731-736 (1990).
Binnie et al., "Parallel Characterization of Bovine von Willebrand Protein (Factor VIII-Associate Protein) by Light Scattering and SDS Gel Electrophoresis," *Thrombosis Research*, 40:523-532 (1985).
Binnie, Cameron Gibson, "von Willebrand Factor and Hirudin: A Study of Two Proteins with an Effect on Coagulation," Dissertation submitted to the University of North Carolina at Chapel Hill (1989). Abstract.
Boeve, et al. "Zeta potential distribution on calcium oxalate crystal and Tamm-Horsfall protein surface analyzed with Doppler electrophoretic scattering." *Journal of Urology.* 152(2 Pt 1), 531-6. (1994) [Abstract only].
Budde et al., "Luminographic Detection of von Willebrand Factor Multimers in Agarose Gels and on Nitrocellulose Membranes," *Thrombosis and Haemostasis*, Stuttgart, DE, 63(2):312-315 (1990).
Budde et al., "von Willebrand Factor and von Willebrand Disease," *Rev Clin Exp Hematol*, 54:335-368 (Dec. 2001).
Cal et al., "Cloning, Expression Analysis, and Structural Characterization of Seven Novel Human ADAMTSs, a Family of Metalloproteinases with Disintegrin and Thrombospondin-I Domains," *Gene*, 283:49-62 (2002).
Cherng, et al. "Effect of size and serum proteins on transfection efficiency of poly ((2-dimetylamino)ethyl methacrylate)—plasmid nanoparticles" *Pharmaceutical Research.* 13(7), 1038-42. (1996) [Abstract only].
Chung et al., "Processing of von Willebrand Factor by ADAMTS-13," *Biochemistry, American Chemical Society*, 41(37): 11065-11070 (Sep. 17, 2002).
Dash et al., "Synthetic Polymers for Vectorial Delivery of DNA: Characterization of Polymer-DNA Complexes by Photon Correlation Spectroscopy and Stability to Nuclease Degradation and Disruption by Polyanions in Vitro," *Journal of Controlled Release*, 48(2,3): 269-276 (Oct. 13, 1997).
Dodd, et al. "Reversible adsorption of soluble hexameric insulin onto the surface of insulin crystals cocrystallized with protamine: and electrostatic interaction." *Pharmaceutical Research.* 12(1), 60-8. (1995) [Abstract only].
Doltchinkova, et al. "Electrokinetic and light scattering properties of pea and Chlamydomonas reinhardtii thylakoid membranes: effect of phytohemagglutinin" *Electrophoresis.* 23(13), 2138-43 (2002) [Abstract only].
Driska, SP. Using light scattering to locate less than a microgram of protein per band in polyacrylamide tube gels after isoelectric focusing. *Analytical Biochemistry.* 260(1), 44-49. (1998) [Abstract only].
Fujikawa et al. "The Mechanism of Activation of Bovine Factor IX (Christmas Factor) by Bovine Factor XIa, Activated Plasma Thromboplastin Atecedent" *Biochemistry* 13: 4508-4516 (1974).
Furlan et al., "Assays of VonWillebrand Factor-Cleaving Protease: A Test for Diagnosis of Familial and Acquires Thrombotic Thrombocytopenic Purpura," *Seminars in Thrombosis and Hemostasis*, Stuttgartm DE, 28(2): 167-172 (Apr. 2002).
Gabriel et al. "Electrophoretic Light Scattering Studies on the Interaction of Fibrinogen with Resting and Activated Human Platelets" *Blood Coagulation Fibrinolysis* 4: 397-403 (1993) [Abstract only].
Gabriel, et al. "Platelet and fibrin modification by radiographic contrast media." *Circulation Research.* 68(3), 881-7. (1991) [Abstract only].
Gao et al., "Capillary Electrophoresis and Synamic Light Scattering Studies of Structure and Binding Characteristics of Protein-Polyelectrolyte complexes," *J. Phys. Chem.* 102:5529-5535 (1998).
Giesen et al. "Blood-Borne Tissue Factor: Another View of Thrombosis" *Proc. Nat'l Acad. Sci.* 96: 2311-2315 (1999) [Abstract only].
Godderz, et al. "Self-association and conformation properties of RAG1: implications for formation of the V(D)J recombinase." *Nucleic Acids Research.* 31(7), 2014-23. (2003) [Abstract only].
Halvorsen et al. "Granulocytes Enhance LPS-induced Tissue Factor Activity in Monocytes Via an interaction with Platelets" *J leukoc Biol* 54: 275-282 (1993).
Hantgan, et al. Biding of a fibrinogen mimetic stabilizes integrin alphaIIbbeta3's open conformation. *Protein Science.* 10(8), 1614-26. (2001) [Abstract only].
Hantgan, et al. Tirofiban blocks platelet adhesion to fibrin with minimal perturbation of GpIIb/IIIa structure. *Thrombosis and Haemostasis.* 87(5), 910-7. (2002) [Abstract only].
Hoffman et al. "Characteristics of The Chemoactic Activity of Heparin Cofactor II Proteolysis Products" *J Leukoc Biol* 265: 156-162 (1990).
Hoffman et al. "Factors IXa and Xa Play Distinct Roles in Tissue Factor-Dependent Initiation of Coagulation" *Blood* 86: 1794-1801.
Hugel, et al. Elevated levels of circulating procoagulant microparticles in patients with paroxysmal nocturnal hemoglobinuria and aplastic anemia. *Blood.* 93(10), 3451-6. (1999) [Abstract only].
International Search Report for PCT/US04/021715; Date of mailing Dec. 16, 2004.

(56) References Cited

OTHER PUBLICATIONS

Jackson, et al. "Analysis of the human replication protein A:Rad52 comples: evidence for crosstalk between RPA32, RPA70, Rad52 and DNA." *Journal of Molecular Biology.* 321(1), 133-48. (2002) [Abstract only].
Johnson, Jr. et al., *Laser Light Scattering*, Dover Press, NY (1994).
Jones, et al. Influence of the subendothelial basement membrane components on fibrin assembly. *Journal of Biological Chemistry.* 263(15), 7043-8. (1988). [Abstract only].
Kirchhofer et al. "Specific Accumulation of Circulating Monocytes and polymorphonuclear Leukocytes on Platelet Thrombi in a Vascular Injury Model" *Blood* 89: 1270-1278 (1997).
Kurachi et al. "Isolation and Characterization of a cDNA Coding for Human Factor IX" *PNAS* 79: 6461-6464(1982).
Lakatos, et al. "Noncovalent interactions in maintaining the native structure of low density lipoprotein" *Biochchemical and Biophysical Research Communications.* 216(1), 414-21. (1995) [Abstract only].
Lawson et al. "Cooperative Activation of Human Factor IX by the Human Extrinsic Pathway of Blood Coagulation" *J Biol Chem* 266: 11317-11327 (1991).
Levy et al., "Mutations in a Member of the ADAMTS Gene Family Cause Thrombotic Thrombocytopenic Purpura," *Nature*, 413:488-494 (2001).
Li et al., "The Physical Exchange of Factor VIII (FVIII) between von Willebrand Factor and Activated Platelets and the Effect of the FVIII B-Domain on Platelet Binding," *Biochemistry*, 36:10760-10767 (1997).
Li, et al. "Transient intermediates in the thrombin activation of fibrinogen. Evidence for only the desAA species." *Journal of Biological Chemistry.* 271(20), 11767-71. (1996) [Abstract only].
Loscalzo et al., "Solution Studies of the Quaternary Structure and Assembly of Human von Willebrand Factor," *Biochemistry*, 24:4468-4475 (1985).
Mannucci et al., "Changes in Health and Disease of the Metalloprotease that Cleaves von Willebrand Factor," *Blood*, 98(9):2730-2735 (2001).
Matsudo, et al. Intramolecular complex formation of poly(N-isopropylacrylamide) with human serum albumin. *Biomacromolecules.* 4(3), 728-35. (2003) [Abstract only].
Matsumoto et al.; "Interaction of proteins with weak amphoteric charged membrane surfaces: effect of PH" *J. Colloid Interface Sci.* 264(1), 82-8 (2003) [Abstract only].
Mauz-Körholz et al., "DDAVP Treatment in a Child with von Willebrand Disease Type 2M," *Eur. J. Pediatr.*, 3:S174-S176 (1999).
McCord et al. "Characterization of the Functional Defect in Factor IX Alabama. Evience for a Conformational Change Due to High Affinity Calcium Binding in the First Epidermal Growth Factor Domain" *J Biol Chem*265: 10254-10259 (1990).
Melton, et al. "Location of the platelet binding site in zymogen coagulation factor IX" *Blood Coagulation Fibrinolysis.* 12(4), 237-43. (2001) [Abstract only].
Miletich et al. "Interaction of Coagulation Factor Xa with Human Platelets" *Proc Natl Acad Sci* 74: 4033-4036 (1977).
Nelsestuen et al. "Elevated Function of Blood Clotting Factor VIIa Mutants That Have Enhanced Affinity for Membranes: Behavior in a Diffusion-Limited Reaction" *J Biol Chem* 276(43): 39825-39831 (2001).
Nemerson "Tissue Factor and Hemostasis" *Blood* 71: 1-8 (1988).
Nesheim et al. "The Binding of 35S-Labeled Recombinant Factor VII to Activated and Unactivated human Platelet" *J Biol Chem*263: 16467-16470 (1988).
Osterud et al. "Activation of Factor IX By the Reaction Product of Tissue Factor and Factor VII: Additional Pathway for Initiating Blood Coagulation" *PNAS* 74: 5260-5264 (1977).
Osterud et al. "Human Blood Coagulation Facto IX. Purification, Properties, and Mechanism of Activation by Activated Factor XI" *J Biol Chem* 253: 5946-5951 (1978).
Rao et al. "The Extrinsic Pathway Inhibitor: A Regulator of Tissue Factor-Dependent Blood Coagulation" *Blood* 75: 1069-1073 (1990).
Rao et al. "Activation of Factor VII Bound to Tissue Factor: A Key Early Tep in the Tissue Factor Pathway of Blood Coagulation" PNAS 85: 6687-6691 (1988).
Rauch at al. "Transfer of Tissue Factor from Leukocytes to Platelets is Mediated by CD15 and Tissue Factor" *Blood* 96:170-175 (2000).
Rawala-Sheikh et al. "Kinetics of Coagulation Factor X Activation by Platelet-bound Factor IXa" *Biochem* 29: 2606-2611 (1990).
Schneppenheim et al., "von Willebrand Factor Cleaving Protease and ADAMTS13 Mutations in Childhood TTP," *Blood*, 101(5):1845-1850 (2003).
Shvetsov, et al. Locking the hydrophobic loop 262-274 to G-actin surface by a disulfide bridge prevents filament formation. *Biochemistry.* 41(35), 10787-93. (2002) [Abstract only].
Slayter et al., "Native Conformation of Human von Willebrand Protein. Analysis by Electron Microscopy and Quasi-Elastic Light Scattering," *The Journal of Biological Chemistry*, 260(14):8559-8563 (1985).
Smejkal et al., "Rapid High-Resolution Electrophoresis of Multimeric von Willebrand Factor Using a Thermopiloted Gel Apparatus," *Electrophoresis*, 24(4): 582-587 (Feb. 2003).
Tracy at al. "Coordinate Binding of Factor Va and Factor Xa to the Unstimulated Platelet" *J Biol Chem* 256(2): 743-751 (1981).
Tracy et al. "Interaction of Coagulation Factor V and Factor Va with Platelet" *J Biol Chem* 254: 10354-10361 (1979).
Tsai, H.M., "Von Willebrand Factor, ADAMTS13 and Thrombotic Thrombocytopenic Purpura." *Journal of Molecular Medicine*, 80(10): 639-647 (Oct. 2002).
Webb, C.E., "Analysis of Von Willebrand Factor (VWF) Multimers in Acquired Haemostatic Disorders," *Ph.D. Council for National Academic Awards (UK)*, 239 pages (1989).
Xia et al., "Electrophoretic and Quasi-Elastic Light Scattering of Soluble Protein-Polyelectrolyte Complexes," *Journal of Physical Chemistry*, 97:4528-4534, 1993.
Xia, et al. Light scattering, CD and ligand binding studies of ferrihemoglobin-polyelectrolyte complexes. *Biopolymers.* 50(2), 153-61. (1999) [Abstract only].
Zheng et al., "Structures of von Willebrand Factor-Cleaving Protease (ADAMTS13), a Metalloprotease Involved in Thrombotic Thrombocytopenic Purpura," *The Journal of Biological Chemistry*, 276(44):41059-41063 (2001).
Zur at al. "Kinetics of Factor IX Activation via the Extrinsic Pathway. Dependence of Km on Tissue Factor" *J Biol Chem* 255: 5703-5707 (1980).
International Search.Report and The Written Opinion of the International Searching Authority for PCT application No. PCT/05/15516 mailed on Nov. 15, 2005.
Li et al. "Transient Intermediates in the Thrombin Activation of Fibrinogen" *The Journal of Biological Chemistry* 271(20): 11767-11771 (1996).
Gabriel et al. "Electrophoretic Light Scattering Studies on the Interaction of Fibrinogen with Resting and Activated Human Platelets" *Blood Coagulation and Fibrinolysis* 4: 397-403 (1993).
Melton et al. "Location of the Platelet Binding Site in Zymogen Coagulation Faction IX" *Blood Coagulation and Fibrinolysis* 12: 237-243 (2001).

\* cited by examiner

ELECTROPHORETIC INTERACTIVE SPECTRAL METHODS AND DEVICES FOR THE DETECTION AND/OR CHARACTERIZATION OF BIOLOGICAL PARTICLES

RELATED APPLICATIONS

This application is a divisional of U.S. patent application Ser. No. 11/121,322 filed May 3, 2005 which claims priority from U.S. Provisional Patent Application Ser. No. 60/568,128, filed May 4, 2004, the disclosures of which are incorporated by reference herein in their entirety.

FIELD OF THE INVENTION

The present invention generally relates to methods and systems for spectroscopy, and more specifically, to electrophoretic interactive spectral techniques.

BACKGROUND OF THE INVENTION

The rapid recognition of the presence of a cell and/or microbe, their specific identification and characterization, the selection of age(s) for therapeutic intervention, and the identification and characterization of specific binding pairs involve clear medical and security needs. The rapid detection of microbes, pathologic or otherwise, in humans, animals or in other environmental locations, such as water, air, or food, may be used to provide an early response, for example, to contain a pathogen and potentially save lives. Due, in part, to the modern centralization of food and drinking supplies, the early detection of microbes in these supplies could improve the safety of food and/or water. As another example, the early and accurate recognition of the presence of a bioterror agent (e.g., ricin, anthrax, ebola, etc.) in a public area could potentially save lives by triggering an early response.

However, current technology generally requires either time-intensive culturing of bacteria or other more expensive assays such as immunological assays (e.g., Enzyme-Linked Immunosorbent Assay "ELISA"). Such technology can be time and/or labor intensive and may be prohibitively expensive.

SUMMARY OF THE INVENTION

According to embodiments of the present invention, methods and systems for identifying a biological particle in a sample medium are provided. An Electrophoretic Quasi-elastic Light Scattering (EQELS) spectrum is generated for the biological particle in the sample medium. The EQELS spectrum is compared to a reference database comprising a plurality of spectra, and each of the plurality of spectra corresponds to an EQELS spectrum for one of a plurality of known biological particles. The biological particle in the sample medium is identified from the comparison. The biological particle can be a biological cell or a microbe selected from the group consisting of viruses, bacteria, fungi, and protozoa.

In some embodiments, the sample medium can be modified and a second EQELS spectrum can be generated for the biological particle in the sample medium after modifying the sample medium. The EQELS spectra can be compared and the biological particle in the sample medium can be characterized based on the comparison. For example, the sample medium can be modified by any of the following: (i) adding a binder for a target biological particle to the sample medium; (ii) adding a solvent to the sample medium; (iii) changing a pH of the sample medium; (iv) changing a temperature of the sample medium; (v) changing an ionic strength of the sample medium; (vi) adding an agent for altering binding of a target biological particle to the sample medium; and/or (vii) adding a complexation agent for a target biological particle to the sample medium. Binders can be added to the sample medium, including antibodies, cells, microbes, ligands, proteins, peptides, nucleic acids, polysaccharides, lipids, lipoproteins, haptens, and/or pharmaceutical compounds.

In particular embodiments, the sample medium includes a fluid selected from the group consisting of: blood, blood products, water, cerebrospinal fluid, ascites, pleural fluid, and synovial fluid. The biological particle can be identified by determining at least one characteristic of the biological particle, such as an electrophoretic mobility, a biological particle concentration, a cytostatic character, a cytotoxic character, a swimming rate, a biological particle volume, a surface charge, a binding strength, a binding constant, a binding profile, a ratio of a swim rate to an electrophoretic mobility, a diffusion constant, a biological particle size, a ratio of a dimension to an electrophoretic mobility, a structure, a gyration ratio, a binding energy, a binding specificity, a binding site mapping, and an enzyme activation on a surface of the biological particle.

In some embodiments, the sample is modified by adding an antibody to the sample medium. The antibody is a specific binder to a predetermined biological particle. The step of characterizing the biological particle includes determining if the biological particle in the sample medium is the predetermined biological particle from the comparison of the first EQELS spectrum and the second EQELS spectrum. As another example, modifying the sample medium can include adding a therapeutic agent to the sample medium. An effectiveness of the therapeutic agent can be assessed based on the comparison of the first EQELS spectrum and the second EQELS spectrum. The comparison can be used to determine whether the therapeutic agent binds to a surface of the biological particle, to determine a change in the swim rate of a microbe, and/or to determine a binding constant for the therapeutic agent.

In some embodiments, the reference database includes swim rates for the plurality of known microbes and a swim rate for the microbe in the sample medium can be determined to identify the microbe. In other embodiments, a microbe can be identified by determining the ratio of the swim rate of the microbe to the electrophoretic mobility of the microbe. The microbe can be identified based on its swim rate.

Detecting an EQELS spectrum can include exposing the biological particles in the sample medium to an electric field, impinging light from a light source on the biological particles in the sample medium to produce scattered light, detecting the scattered light, and detecting a Doppler shift in the scattered light compared to light from the light source.

In particular embodiments, the biological particle is collected using a filtration device. A gas and/or liquid can be filtered with a filter to trap the biological particle, and the filter can be flushed with a fluid to provide the sample medium. The biological particle can be collected automatically.

In further embodiments according to the present invention, methods for detecting a presence or absence of a specific binding pair in a sample medium are provided. The specific binding pair includes a first member and a second member. A first EQELS spectrum of the sample medium is detected. The sample medium includes the first member of the specific binding pair. A specimen is added to the sample medium. A second EQELS spectrum of the sample medium is detected after adding the specimen to the sample medium. The first EQELS spectrum and the second EQELS spectrum are compared, and the presence or absence of the second member of the specific binding pair in the sample medium is detected from the comparison. The first member of the specific binding pair can be a biological particle, such as a microbe or biological cell.

In some embodiments, a first electrophoretic mobility of the first member of the specific binding pair is determined from the first EQELS spectrum, and a second electrophoretic mobility of the first member of the specific binding pair is determined from the second EQELS spectrum. The first EQELS spectrum and the second EQELS spectrum are compared by comparing the first electrophoretic mobility and the second electrophoretic mobility.

In particular embodiments, a binding constant for the specific binding pair is determined. Whether the first member of the specific binding pair is activated and/or whether the first member of the specific binding pair experiences cell death can also be determined. The specimen can be a drug, and a therapeutic and/or toxic effect of the drug can be determined from the comparison of the first EQELS spectrum and the second EQELS spectrum.

According to further embodiments of the present invention, methods of assessing a biological particle in a medium include detecting an EQELS spectrum of the biological particle in the sample medium. The EQELS spectrum is compared to a reference database comprising a plurality of spectra. Each of the plurality of spectra correspond to an EQELS spectrum for one of a plurality of known particles. A characteristic of the biological particle is assessed based on the comparison. For example, a diseased cell can be detected. In particular embodiments, the sample medium is a specimen of blood.

According to still further embodiments of the invention, systems for identifying a biological particle in a sample medium include an EQELS spectrometer comprising and EQELS controller configured to detect an EQELS spectrum for the biological particle in the sample medium. The biological particle can be a biological cell or a microbe. An EQELS analyzer is in communication with the EQELS spectrometer. A reference database is in communication with the EQELS analyzer. The reference database includes a plurality of spectra, and each of the plurality of spectra corresponding to an EQELS spectrum for one of a plurality of known biological particles. The EQELS analyzer is configured to compare the EQELS spectrum for the biological particle in the sample medium from the EQELS spectrometer with the plurality of spectra from the reference database and to identify the biological particle in the sample medium from the comparison.

According to further embodiments of the invention, systems for detecting a presence or absence of a specific binding pair in a medium are provided. The specific binding pair includes a first member and a second member. An EQELS spectrometer includes an EQELS controller. The EQELS controller is configured to detect a first EQELS spectrum of the sample medium. The sample medium includes the first member of the specific binding pair. A sample modification system is in communication with the EQELS controller and configured to add a specimen to the sample medium. The EQELS controller is configured to detect a second EQELS spectrum of the sample medium from the EQELS spectrometer after the sample modification system adds the specimen to the sample medium. An EQELS analyzer is in communication with the EQELS spectrometer and is configured to compare the first EQELS spectrum and the second EQELS spectrum and to detect the presence or absence of the second member of the specific binding pair in the sample medium from the comparison.

According to further embodiments of the invention, systems of assessing a biological particle in a sample medium include an EQELS spectrometer configured to detect an EQELS spectrum of the biological particle in the sample medium. An EQELS analyzer includes a reference database comprising a plurality of EQELS spectra. Each of the plurality of spectra correspond to an EQELS spectrum for one of a plurality of known biological particles. The EQELS analyzer is configured to compare the EQELS spectrum of the sample medium to the plurality of spectra in the reference database and to assess a characteristic of the biological particle based on the comparison.

DETAILED DESCRIPTION OF THE INVENTION

Figure 1:
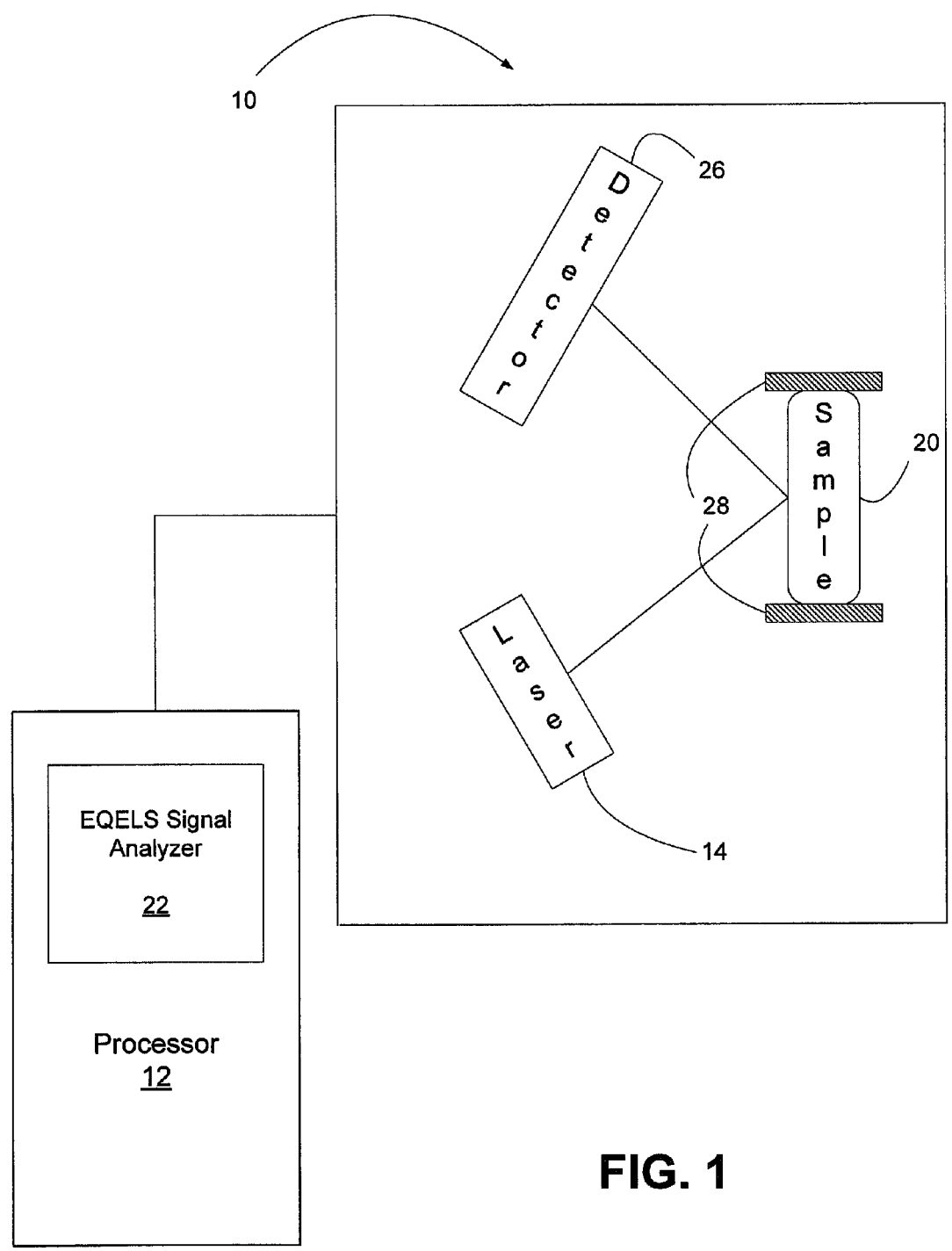
FIG. 1 is a block diagram of an Electrophoretic Quasi-elastic Light Scattering (EQELS) spectrometer according to embodiments of the present invention.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. Elements in the various figures are not drawn to scale and may be enlarged to show detail.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

"Target" as used herein refers to any type of particle for which detection may be desired, including but not limited to biological particles, e.g., whole cells, microbes, peptides, proteins, nucleic acids, polysaccharides, lipids, lipoproteins, etc.

"Binding pair" refers to a pair of particles, one of which may be a target, which members of the binding pair specifically and selectively bind to one another. Examples of suitable binding pairs include, but are not limited to: cells and ligands; microbes and ligands; nucleic acid and nucleic acid; protein or peptide and nucleic acid; protein or peptide and protein or peptide; antigens and antibodies; receptors and ligands, haptens, or polysaccharides, complementary nucleic acids, pharmaceutical compounds, etc. Members of binding pairs are sometimes also referred to as "binders" herein.

The term "microbe" as used herein refers to viruses, bacteria, fungi, and/or protozoa.

The term "cell" as used herein refers to any type of cell, including human cells, animal cells (such as swine cells, rodent cells, canine cells, bovine cells, ovine cells and/or equestrian cells) cloned cells, plant cells, or the like. The cells may be blood cells, cultured cells, biopsied cells, or cells that are fixed with a preservative. The cells can be nucleated, such as white blood cells or suspended endothelial cells, or non-nucleated, such as platelets or red blood cells.

The following abbreviations are used herein: Recombinant activated coagulation factor VIIa (rFVIIa), Wild-type coagulation factor VIIa (FVIIa) tissue factor (TF), Coagulation factor IX (FIX), Activated coagulation factor IX (FIXa), Coagulation factor VIII (FVIII), Coagulation factor X (FX), Coagulation factor XI (FXI), Activated coagulation factor XI (FXIa), binding constant (Kd), prostacyclin (PGI2), platelet rich plasma (PRP), electrophoretic mobility ($\mu$), change in electrophoretic mobility ($\Delta\mu$), Confidence interval (CI), Standard error (SE).

While the methods and apparatus of the present invention are sometimes explained with respect to analyte and receptor binding pairs herein for purposes of clarity, it is to be understood that the methods and apparatus of the instant invention may be applied to other targets, probes, and other binders.

Although embodiments of the present invention are describe with respect to Electrophoretic Quasi-elastic Light Scattering (EQELS) spectroscopy it should be understood that other electrophoretic interaction spectral techniques (i.e., techniques in which a biological particle in an electrophoretic field interacts with an energetic medium to generate a spectrum) can be used, such as dynamic light scattering (DLS) and photon correlation spectroscopy (PCS). Although embodiments of the present invention are describe are with respect to an excitation light beam, other energetic media can be used, including electromagnetic energy, acoustic energy, ultrasonic energy, or other suitable energy media. For example, electromagnetic energy can be employed from any suitable spectral range, such as visible light, infrared, ultraviolet, and/or x-ray ranges. For example, actinic radiation having a wavelength from about 200 nm to about 700 nm can be used as an energetic medium for interaction with a biological particle in an electrophoretic field. Visible light radiation can be used in light-scattering techniques, including elastic light scattering and quasi-elastic light scattering. Ultraviolet radiation can be used, for example, in capillary electrophoresis systems having an ultraviolet laser as an energy source for ultraviolet radiation impinged on a biological particle in the capillary flow stream. Thus, any suitable energy source and corresponding energy medium can be used.

According to particular embodiments of the present invention, Electrophoretic Quasi-elastic Light Scattering (EQELS) spectroscopy is used to identify a microbe in a medium and/or to detect the presence or absence of a specific binding pair in a medium. Electrophoretic quasi-elastic light scattering is a laser spectroscopy technique generally used to study the electrophoretic mobility of particles in a sample. An exemplary EQELS spectrometer 10 is illustrated in FIG. 1. The spectrometer 10 includes a laser 14 that impinges a beam of light onto a sample 20. The sample 20 is positioned between two electrodes 28 that provide an electric field to the sample 20. Charged particles in the sample 20 are induced to move due to the application of the electric field. For example, the sample 20 can include a sample medium in which a biological particle of interest is in a solution or suspension. For example, the sample medium can include blood, blood products, water, cerebrospinal fluid, ascites, pleural fluid, and/or synovial fluid. Movement of the particles in the sample 20 is detected by quasi-elastic scattering from the generally coherent light provided by the laser 14. Some of the incident photons will encounter moving particles in the sample 20. When this encounter occurs, a small amount of energy from the photon is given up, and consequently, the frequency of the scattered light is slightly reduced. This scattered light is detected by a detector 26.

As illustrated in FIG. 1, the spectrometer 10 is connected to a processor 12 that includes an EQELS signal analyzer 22.

The processor 12 receives signals from the spectrometer 10, which are analyzed by the EQELS signal analyzer 22. For example, the scattered light detected by the detector 26 can be analyzed to determine the magnitude of the small shift in frequency. This shift in frequency is proportional to the rate of movement of the particle in the sample 20 and is detected as a Doppler shift. The signal analyzer 22 can measure the Doppler shift through a heterodyne technique in which unshifted light is mixed with the scattered light to produce "beats". This signal is measured as an autocorrelation function that can then be Fourier transformed to yield a power spectrum for interpretation.

In some embodiments, the EQELS spectrometer 10 can be used to detect and/or characterize biological particles, such as biological cells and/or microbes.

In particular embodiments, the EQELS spectrometer 10 is used to detect an EQELS spectrum for a sample 20 that includes a biological particle in a sample medium. The EQELS spectrum is compared to a database of known spectra, each of the known spectra corresponding to one of a plurality of known biological particles. The biological particle in the medium is identified from the comparison.

In other specific embodiments, the presence or absence of a specific binding pair in a sample medium is detected by the EQELS spectrometer 10. A first EQELS spectrum of a sample medium including one member (e.g., the target) of the specific binding pair is detected. A specimen is added to the sample medium and a subsequent EQELS spectrum is detected after adding the specimen. The EQELS spectra before and after the addition of the specimen are compared, and the presence or absence of the second member of the specific binding pair in the sample medium is detected based on the comparison.

In further particular embodiments, a biological particle is assessed. The EQELS spectrometer 10 is used to detect an EQELS spectrum for a sample 20 that includes a biological particle. The EQELS spectrum is compared to one or more known spectra of known biological particles. A characteristic of the biological particle can be assessed, such as diseases or abnormalities, including congenital, neoplastic or other conditions. Various characteristics can be used to assess the biological particle, including electrophoretic mobility, the concentration of the biological particle, cytostatic character, cytotoxic character, swimming rate, particle volume, surface charge, binding strength, binding constant, binding profile, a ratio of the swim rate to the electrophoretic mobility ratio, diffusion constant, particle size, a ratio of the dimension of the particle to the electrophoretic mobility, structure factors, gyration ratio, binding energy, binding specificity, binding site mapping and/or enzyme activation on a surface of the biological particle.

Figure 2:
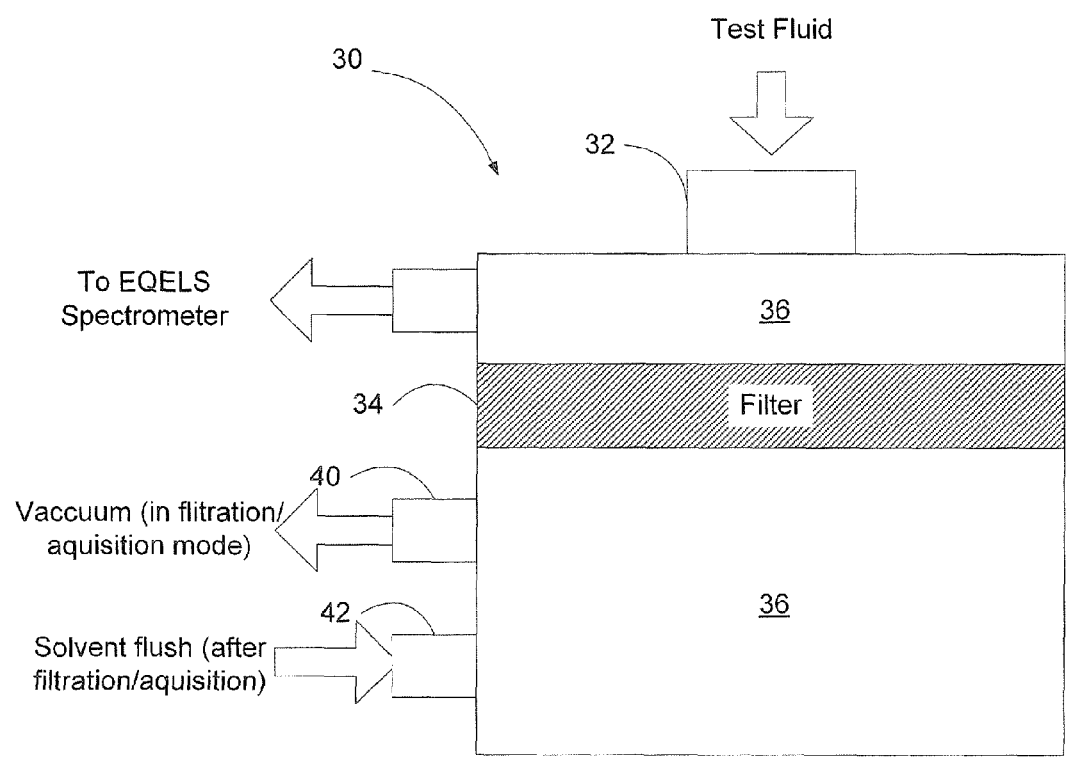
FIG. 2 is a block diagram of a specimen acquisition system according to embodiments of the present invention.

FIG. 2 is a block diagram of a sample acquisition system 30 according to embodiments of the present invention. The acquisition system 30 includes an acquisition chamber 36 that includes a filter 34, inlets 32 and 42 and outlets 38 and 40. Valves (not shown) can be used to control flow between the inlets 32 and 42 or the outlets 38 and 40 and the chamber 36. In the configuration shown in FIG. 2, a vacuum can be provided in outlet 40 to create negative pressure in the chamber 36 so that test fluid enters the chamber 36 from the inlet 32. The test fluid can be a gas or liquid, such as air or water. The test fluid then passes through the filter 34, and microbes and/or cells are filtered from the test fluid. After a specimen is collected on the filter 34, a solvent enters the chamber 36 through the inlet 42. The solvent can combine with microbes and/or cells that have been collected on the filter to form a medium. The medium then exits the chamber through the outlet 38 to a collection area for subsequent EQELS spectroscopy or directly to an EQELS spectrometer. Although two inlets 32 and 42 and two outlets 38 and 40 are shown in FIG. 2, it should be understood that other configurations can be used to accomplish the functions described herein. For example, the outlet 40 and the inlet 42 can be combined to provide a single inlet/outlet.

The acquisition system 30 in FIG. 2 can be used to automatically collect a sample for analysis from a fluid. For example, the acquisition system 30 could be miniaturized, automated and/or combined with an EQELS spectrometer and placed in various locations to monitor an air, water, and/or food supply. The acquisition system 30 can be used for bioterror surveillance to collect samples of fluids in an environment and/or monitor the collected samples for microbial agents. A telecommunications system can also be provided to communicate the results of the EQELS spectra obtained. When a EQELS spectrum is obtained that indicates the presence of a particular microbe is in the sample, a central command can be alerted through the telecommunications system and/or an alarm can be activated.

The acquisitions system 30 can also be used to add various antibodies to the collected sample. For example, a pre-selected antibody with antigenic specificity against pathogens of bioterror significance could be added to a medium including the suspected microbe in the chamber 36, e.g., through the inlet 42. If the suspected microbe were present in the sample, the antibody may selectively modify the microbe's mobility. The change in mobility can be detected by a change in the EQELS spectra obtained before and after the addition of the antibody.

Figure 3:
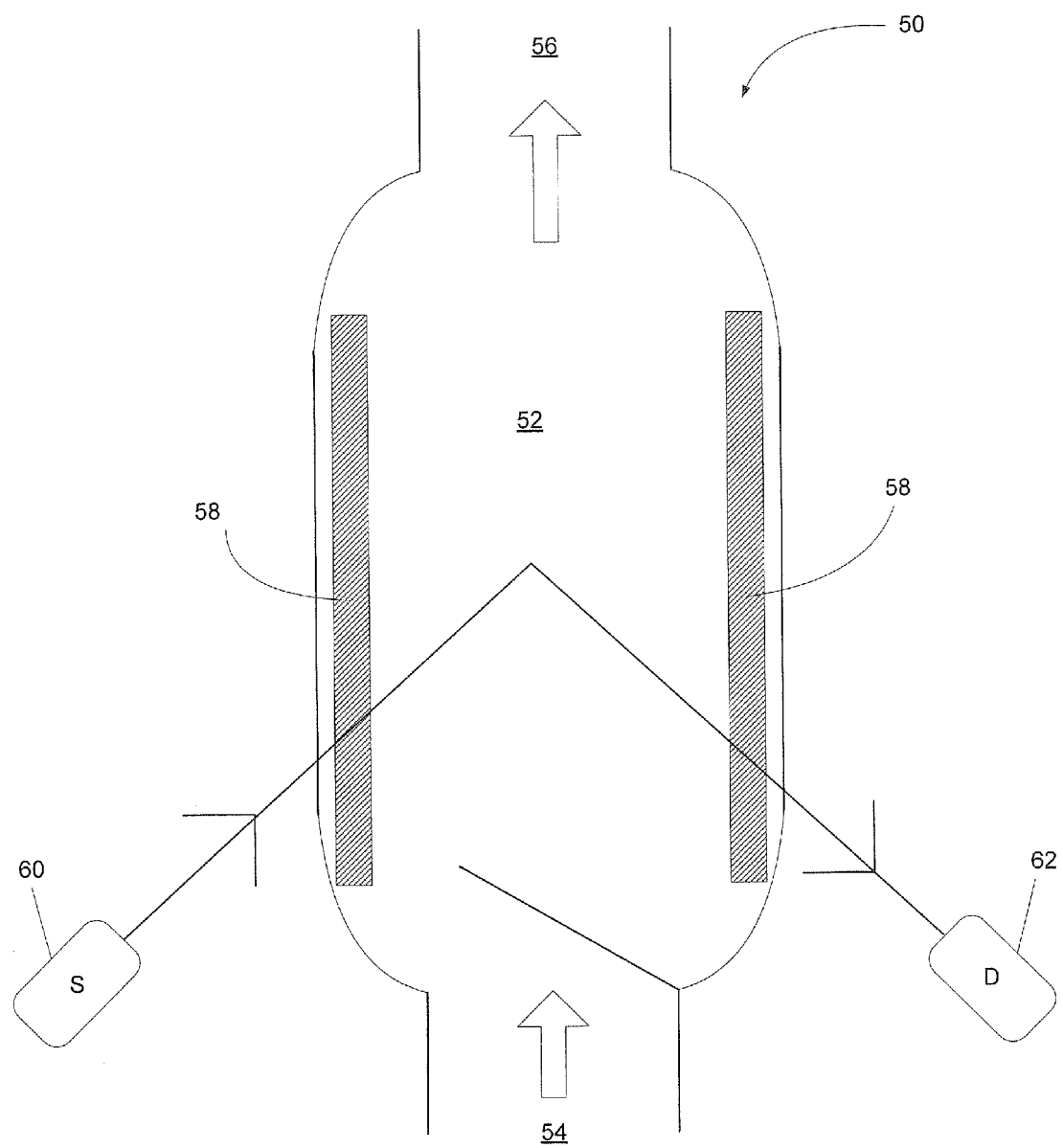
FIG. 3 is a block diagram of a flow-through EQELS spectrometer according to embodiments of the present invention.

In particular embodiments according to the present invention, a flow-through device 50 can be provided as illustrated in FIG. 3. The flow-through device 50 includes an inlet 54 and outlet 56 and a sample region 52 therebetween. The inlet 54 can include a valve (not shown) for controlling the flow of a sample medium into the sample region 52. Electrodes 58 are positioned on opposite sides of the sample region 52 to produce an electric field. A light source 60 impinges a light beam on the sample region. The resulting scattered light is then detected by a detector 62.

As illustrated in FIG. 3, a sample medium including a microbe and/or cell of interest can flow into the sample region 52 through the inlet 54. The inlet 54 can be closed, for example, using a valve (not shown), when a suitable amount of sample medium has entered the sample region 52. The electrodes 58 can produce an electric field in the sample region 52, and an EQELS spectrum can be obtained using the incident light from the light source 60 and scattered light from the detector 62. The sample medium can then exit the sample region 52 through the outlet 56, for example, using a fluid pump, suction mechanism, and/or other techniques to remove fluid from a chamber including techniques known to those of skill in the art. The outlet 56 can also include a valve (not shown) for controlling and directing fluid flow from the sample region 52. Another sample medium can then flow through the inlet 54 for subsequent testing. In this configuration, several sample mediums can be tested in rapid succession. In some embodiments, the flow-through device 50 can be connected to the acquisition system 30 in FIG. 2. It should be understood that other configurations of flow-through devices can be used to perform operations according to embodiments of the present invention. For example, the inlet 54 and the outlet 56 can be replaced with a single opening to provide a combined inlet/outlet for batch-type operation.

Figure 4:
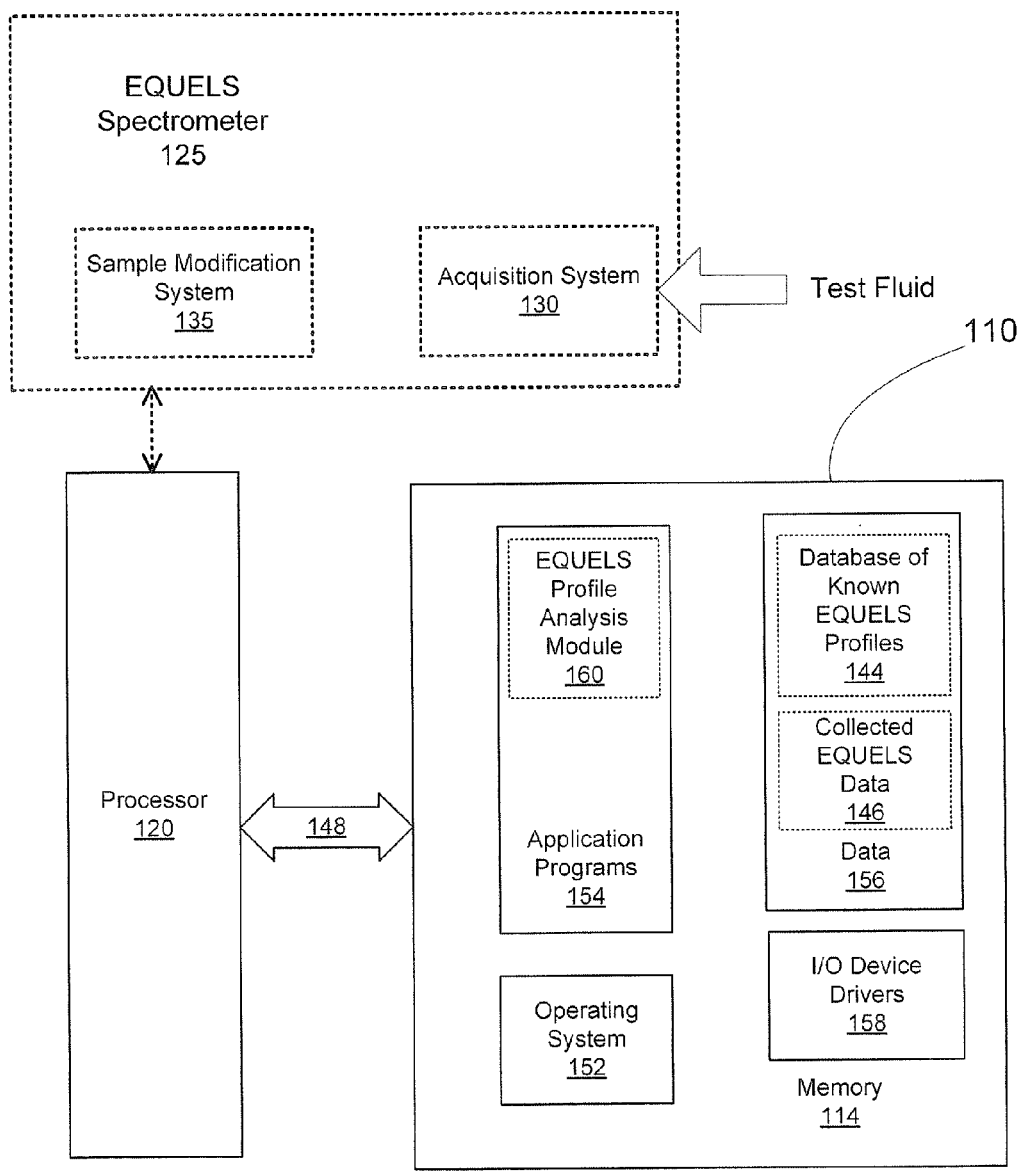
FIG. 4 is a block diagram of data processing systems according to embodiments of the present invention.

FIG. 4 is a block diagram of exemplary embodiments of data processing systems that illustrates systems, methods, and computer program products in accordance with embodiments of the present invention. A data processing system 110 is provided that includes a processor 120 in communication with an EQELS spectrometer 125, and a memory 114. Exemplary EQELS systems that can be used for the EQELS system 125 are illustrated in FIGS. 1 and 3. As illustrated in FIG. 4, the EQELS system 125 includes an acquisition system 130 and a sample modification system 135. The sample modification system 135 is configured to modify the sample in the spectrometer, such as by adding a substance, such as an antibody or a therapeutic agent, to the sample. An exemplary acquisition system for acquiring a specimen for EQELS spectrometry is illustrated in FIG. 4. In some embodiments, the EQELS spectrometer 125, the sample modification system 135 and/or the acquisition system 130 are omitted. For example, a sample can be positioned in an EQELS system 125 manually without requiring a separate acquisition system 130 and/or spectra can be obtained according to embodiments of the invention without modifying the sample with the sample modification system 135. In some embodiments, the EQELS spectrometer 125 is omitted and an EQELS spectrum obtained from a remote EQELS spectrometer is provided to the data processing system 110 for analysis.

The sample modification system 135 can modify the sample, for example, by adding a binder for a target biological particle, adding a solvent, changing the pH of the sample medium, changing the temperature of the sample medium, changing the ionic strength of the sample medium, adding an agent for altering the binding characteristics of a target biological particle, and/or adding a complexation agent for a target biological particle. Examples of binders, include antibodies, cells, microbes, ligands, proteins, peptides, nucleic acids, polysaccharides, lipids, lipoproteins, haptens, and pharmaceutical compounds.

The processor 120 communicates with the memory 114 via an address/data bus 148. The processor 120 can be any commercially available or custom microprocessor. The memory 114 is representative of the overall hierarchy of memory devices containing the software and data used to implement the functionality of the data processing system 110. The memory 114 can include, but is not limited to, the following types of devices: cache, ROM, PROM, EPROM, EEPROM, flash memory, SRAM, and DRAM.

As shown in FIG. 4, the memory 14 may include several categories of software and data used in the data processing system 110: the operating system 152; the application programs 154; the input/output (I/O) device drivers 158 and the data 156. The data 156 may include a database of known EQELS profiles 144 and/or EQELS data 146 from the EQELS system 125.

As will be appreciated by those of skill in the art, the operating system 152 may be any operating system suitable for use with a data processing system, such as OS/2, AIX, OS/390 or System390 from International Business Machines Corporation, Armonk, N.Y., Windows CE, Windows NT, Windows95, Windows98, Windows2000, or WindowsXP from Microsoft Corporation, Redmond, Wash., Unix or Linux or FreeBSD, Palm OS from Palm, Inc., Mac OS from Apple Computer, LabView or proprietary operating systems. The I/O device drivers 158 typically include software routines accessed through the operating system 152 by the application programs 154 to communicate with devices such as I/O data port(s), data storage 156 and certain components of the memory 114 and/or the EQELS spectrometer 125. The application programs 154 are illustrative of the programs that implement the various features of the data processing system 110 and preferably include at least one application which supports operations according to embodiments of the present invention. The data 156 represents the static and dynamic data used by the application programs 154, the operating system 152, the I/O device drivers 158, and other software programs that may reside in the memory 114.

While the present invention is illustrated, for example, with reference to the EQELS profile analysis module 160 being an application program in FIG. 4, as will be appreciated by those of skill in the art, other configurations may also be utilized while still benefiting from the teachings of the present invention. For example, the EQELS profile analysis module 160 may also be incorporated into the operating system 152, the I/O device drivers 158 or other such logical division of the data processing system 110. Thus, the present invention should not be construed as limited to the configuration of FIG. 4, which is intended to encompass any configuration capable of carrying out the operations described herein.

The I/O data port can be used to transfer information between the data processing system 110 and the EQELS spectrometer 125 or another computer system or a network (e.g., the Internet) or to other devices controlled by the processor. These components may be conventional components such as those used in many conventional data processing systems that may be configured in accordance with the present invention to operate as described herein.

Particular embodiments of the present invention can be used to detect bioterror agents in an environment that may be susceptible to the presence or incursion of such agents, such as air, water, or food supplies, or in human or animal tissue. A sample of material from the environment of interest can be used to obtain an EQELS spectrum, and the bioterror agent can be identified and/or characterized by comparing the EQELS spectrum to a reference database of EQELS spectra of candidate agents to determine if the environment contains any of the candidate agents.

Embodiments according to the present invention will now be described with respect to the following non-limiting examples:

Example 1

Microbe Detection

Figure 5:
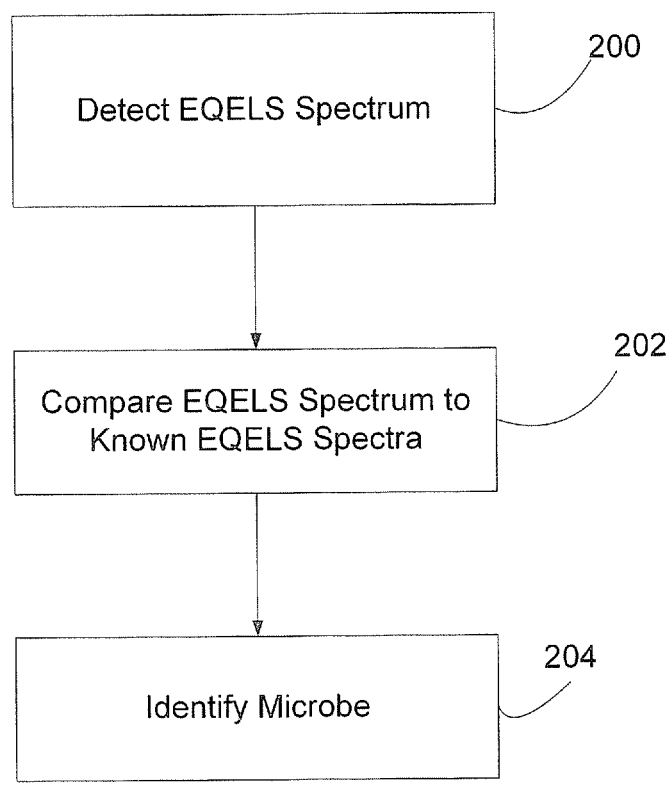
FIGS. 5-7 are flow charts illustrating operations according to embodiments of the present invention.

As shown in FIG. 5, an EQELS spectrometer (such as the EQELS spectrometer 10 in FIG. 1) can be used to detect an EQELS spectrum for a sample that includes a microbe in a medium (Block 200). The EQELS spectrum may be compared to a database of known spectra such that each of the known spectra corresponds to one of a plurality of known microbes (Block 202). The microbe in the medium can be identified from the comparison (Block 204). Microbes include viral, bacterial, fungal and protozoa microbes, and in particular embodiments, cytomegolovirus (CMV), herpes simplex virus (HSV), Epstein-Barr virus (HBV), respiratory syncytial virus (RSV) and human immunodeficiency virus (HIV).

For example, the EQELS spectrum can be used to determine the electrophoretic mobility of a microbe, and the electrophoretic mobility can be used to identify the microbe. The electrophoretic mobility may depend on the surface charge of the microbe and/or on frictional forces resulting from the shape/size of the microbe and/or on the viscosity of the solvent. The surface charge on the microbe surface may also depend on solvent conditions, such as pH.

In some embodiments, the concentration of a microbe can be determined. The EQELS spectrum from a sample with an unknown microbial concentration can be compared with a spectrum from a sample with a known concentration. The integration of the spectrum (i.e., the area-under-the-curve) can be used to determine the concentration.

The proof of the microbe's identity may be enhanced by the addition of an antibody that binds to a specific microbe. When the antibody binds to the microbe, it can change both the surface charge and/or the frictional forces and thus, the antibody can change the electrophoretic mobility of the microbe. The electrophoretic mobility can be determined from the EQELS spectrum.

Embodiments of the present invention can be used to identify a microbe, for example, used for bioterror. A specific list of potential microbe pathogens could be developed. If an initial screen of the sample showed the presence of a microbe, a cocktail of antibodies that included antibodies against microbes-of-interest would be added to the sample. If any change in the profile of the original mobility is observed, then the presence of a microbe could be identified.

The sensitivity of a specific antibiotic or anti-microbial agent against a specific microbe can also be determined. Without wishing to be bound by any particular theory, before an antibiotic or anti-microbial agent can exert its therapeutic effect, it must first bind to the surface of the microbe. When the antibiotic or anti-microbial agent binds to the surface, it can change the microbe surface charge and/or frictional forces. An EQELS spectrum or spectra can be used to detect the changes in surface charge and/or frictional forces. Moreover, if the antibiotic or anti-microbial agent is effective in producing either a cytostatic effect or in killing the microbe, an effect on the swimming rate of the microbe, the surface charge, and/or the microbe's volume (e.g., from swelling) may be observed. Thus, EQELS spectra can be used to determine whether an antibiotic or anti-microbial agent binds to a microbe and/or kills the microbe. This information may be useful to test a microbial sample for sensitivity to a particular antibiotic or anti-microbial agent.

The binding constant for an anti-microbial agent can also be determined from an EQELS spectrum of a sample including the microbe and the anti-microbial agent. The binding constant can be used as an indication of the effectiveness of therapy for the anti-microbial agent. For example, the concentration of the anti-microbial agent can be increased over time in the microbial sample medium. Changes in the mobility of the microbe as a function of the therapeutic agent can then be determined from the EQELS spectrum. The resulting binding profile can be fitted to a binding model, such as a one-state-binding model and/or a higher state binding model, to provide a binding constant.

Parameters that can be used to identify microbes and/or to assess the effectiveness of an anti-microbial agent include swim rate (e.g., as determined by laser velocimetry), the ratio of the microbe swim rate to the electrophoretic mobility, the diffusion constant, the dimensions of the microbe (e.g., as determined by the diffusion constant and/or including ratios of gyration, volume, characteristic dimension, structure factors, rod/cocci/axial ratios, etc.), and/or the ratio of a microbe dimension (e.g., the largest dimension) and the electrophoretic mobility.

Examples of fluids for which EQELS spectrum can be obtained and various microbes in the sample assessed include blood, blood products, water, air, cerebrospinal fluid, ascites, pleural fluid, synovial fluid and the like.

Example 2

Cellular-Based Assays and Cellular Monitoring

Figure 6:
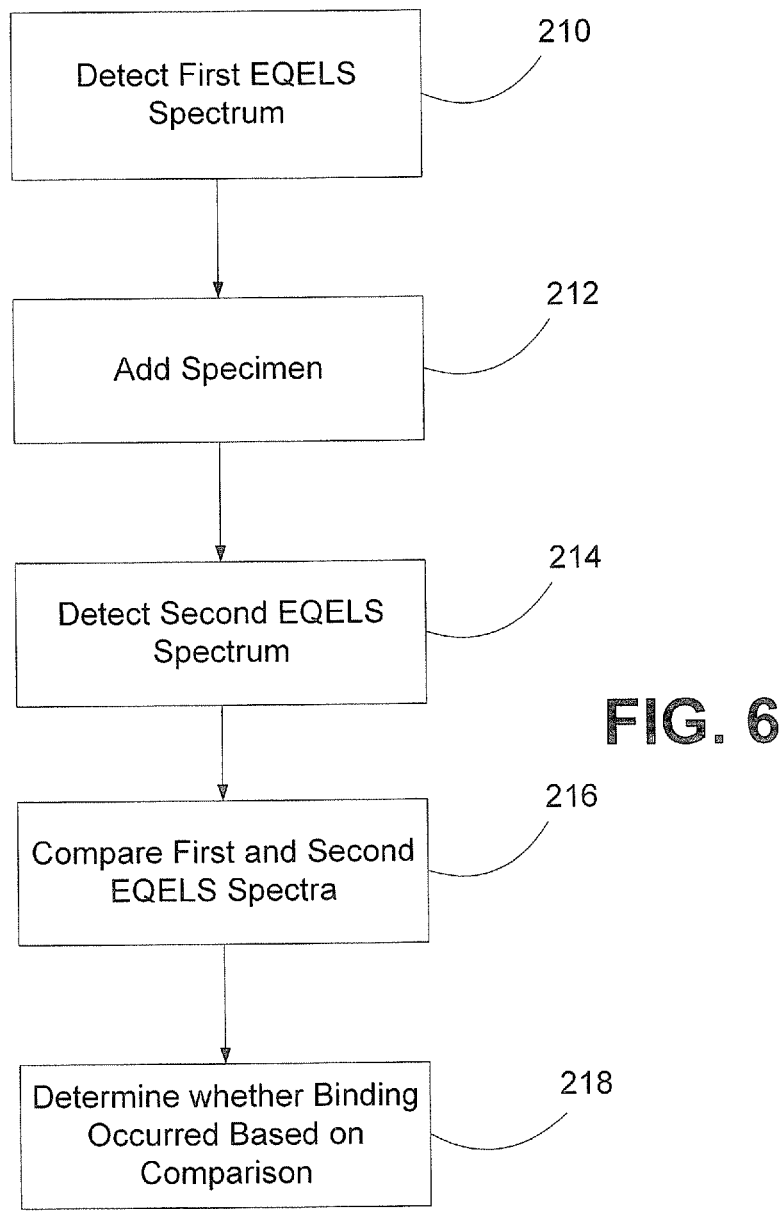

In some embodiments, the presence or absence of a specific binding pair in a medium is detected by an EQELS spectrometer (such as the EQELS spectrometer 10 in FIG. 1). As illustrated in FIG. 6, an initial EQELS spectrum of a medium including one member of the specific binding pair (e.g., a cell) is detected (Block 210). A specimen is added to the medium (Block 212) and a subsequent EQELS spectrum is detected after adding the specimen (Block 214). The EQELS spectra before and after the addition of the specimen are compared (Block 216), and the presence or absence of the other member of the specific binding pair in the medium is detected based on the comparison (Block 218). The other member of the specific binding pair can include any ligand that binds to a cell surface, including chemical or biologic drugs and/or naturally occurring or man-made substances, such as growth factor, hormones, lymphokines, chemokines, lipids, antibodies, biochemicals and the like. A change in the measured cell electrophoretic mobility can be detected based on the EQELS spectra before and after the addition of the specimen when specific binding occurs.

Figure 7:
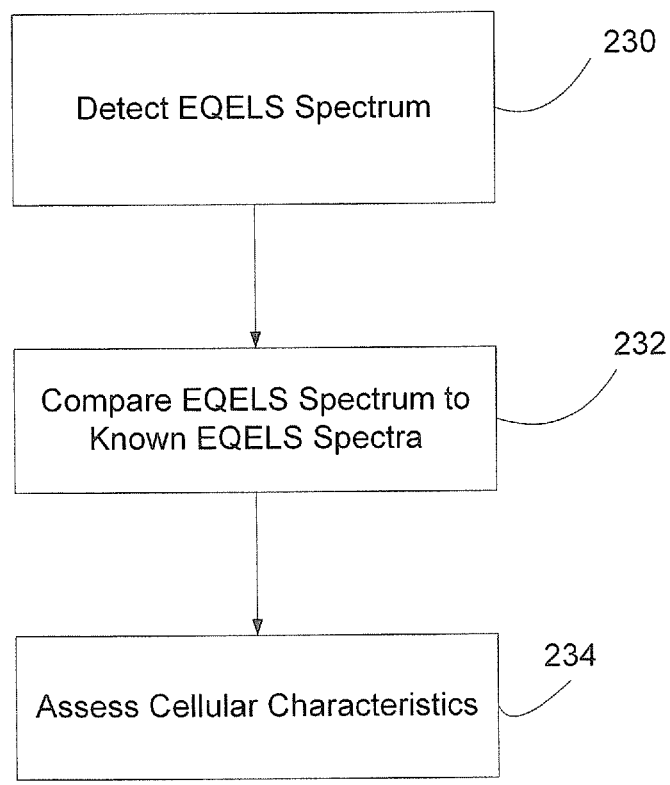

In other embodiments, a cellular specimen is assessed. As illustrated in FIG. 7, an EQELS spectrometer, such as the EQELS spectrometer 10 in FIG. 1, is used to detect an EQELS spectrum for a sample that includes a cellular specimen (Block 230). The EQELS spectrum is compared to one or more known spectra of known cells (Block 232). A characteristic of the cellular specimen can be assessed (Block 234), such as diseases or abnormalities, including congenital, neoplastic or other conditions.

Differences in electrophoretic mobility detected by EQELS spectrometry can be used to detect abnormal cells, normal cell binding therapeutics or an abnormal ligand, and/or to provide detailed thermodynamic, biologic, clinical, and chemical information concerning cellular interaction. Examples of characteristics that can be assessed include binding constants, binding energies, binding specificity, and/or mapping of binding cites. For example, EQELS spectra can detect a change in the electrophoretic mobility of a cell that is induced by ligand binding. The ligand binding constant can be obtained from the dependence of the change in the cell electrophoretic mobility on the concentration of the ligand. The binding constant is a useful property of the ligand-cell interaction that can be related to the biological efficacy of the ligand, mapping of a binding site, and/or the selection of a therapy.

For example, cells derived from a specific developmental cell line can express different surface epitopes. These differences can contribute to the identification of a cell as a lymphocyte, granulocyte, T-cell, B-cell etc. This cell surface property results in different EQELS spectra that can be used to differentiate between leukemic blasts and normal blood cells, between platelets and red blood cells, etc. Embodiments of the present invention can detect these differences without using fixed (preserved) cells, incubation with a fluorescently labeled antibody, and/or a flow cytometry technique.

In some cases, ligand binding can lead to cell activation, such as with thrombin (or other platelet agonists) binding by platelets and FinetLuePhe binding by neutrophilic granulocytes. Another example of cell activation is the activation of leukocytes. When a cell is activated, its surface changes to expose a different array of biologic molecules. These changes can result in a measurable difference in the cell surface charge and, hence, its electrophoretic mobility. When a cell dies, similar events can occur, including the loss of electrochemical gradients across the cell membrane. These events may be detected by changes in the EQELS spectra.

Without wishing to be bound by any particular theory, each type of tissue includes cells that has unique surface characteristics. The uniqueness of the cell surface results from the expression of the molecular species on the cell's surface that permits the unique function and ability for each cell line. If a given cell binds a ligand to its surface or if the cell line becomes diseased, either through a congenital disease or an acquired disease, its cell surface changes. A change in the cell surface can lead to changes in the cell's surface charges. An EQELS spectrum can be used to detect a change in the cell surface charge. The EQELS spectrum can also be used to detect specific drug binding, to detect the activation of enzymes on the cell surface, to distinguish normal cells from abnormal cells, to distinguish resting cells from activated cells, and/or to monitor drug efficacy and safety.

For any cellular therapeutic to be effective, it must first bind to a targeted cell surface. Therapeutic agents can include any ligand or drug. The avidity or strength with which a therapeutic agent binds to the cell often determines its usefulness or efficacy as a therapeutic agent. The interaction between a therapeutic agent and the cell(s) can be assessed. The information that can be obtained from an EQELS spectrum includes, without limitation, the nature of the biologic interaction, the chemical interaction, and/or the thermodynamic interaction between the therapeutic agent and a targeted cell surface. In addition to the determination of cellular binding of the therapeutic agent, the binding constant and factors that effect binding, such as the concentration of the agent, temperature, pH, ionic strength, competing agents (including inhibitors of binding) can be determined.

The differences in normal and abnormal cells can be detected using a comparison of EQELS spectra. For example, platelets with congenital abnormalities, such as Glantzmann's thromboesthinia or the Benard-Soulier syndrome, bind to certain ligands abnormally, and this abnormal binding may be detected in a EQELS spectrum before and after the ligand is added to a platelet medium. Leukemic blasts can also be differentiated from normal blasts by comparing a EQELS spectrum of normal blasts to an EQELS spectrum of Leukemic blasts. The production by the host of an abnormal product, such as a monoclonal antibody or a polyclonal antibody, can also be detected.

Example 4

Drug Developments

The efficacy of various types of therapeutic agents on a microbe and/or a cell can also be assessed. An EQELS spectrum can be obtained from a sample before and/or after a therapeutic agent is administered. Therapeutic agents that may be assessed in this manner include drugs, hormonal agents, leukemic therapeutics, anti-platelet effects, pharmacological agents, vitamins, pH conditions or analytes. The systems and methods of the present invention may also be used to evaluate, adjust and/or identify therapies in drug/treatment development programs and/or in clinical or pre-clinical drug trials or other drug development testing, including clinical or pre-clinical trials for developing or evaluating vitamin supplements, herbal remedies, and/or other treatments. Embodiments of the present invention may also be used to evaluate, adjust and/or identify a suitable dose of a selected treatment based on the effectiveness of the treatment as measured by EQELS spectra. Patient specific assessments can be made to select appropriate therapeutic agents. In some embodiments, no reporter label is required, and the process is non-destructive to either the cell under study or to the ligand.

During the development of a drug, the chemical structure of the drug can be refined. Thus, large numbers of drugs may be screened before the selection of the lead compound. This same process can be applied to the development of biologics. Embodiments of the invention can be used to evaluate the efficacy of various compounds, including peptides, proteins, lipids, nucleic acids, and/or small molecules. Examples of interactions that can be evaluated using one or more EQELS spectra include the binding of coagulation factors to activated platelets, the inhibition of platelet agonists, the selective binding to neoplastic tissue compared to normal tissue, surface activation and/or enzymes interaction. The detection of therapeutic agent and cell or microbe interaction and the assessment of the biologic, chemical and/or thermodynamic character of the binding can be used to select promising therapeutic agents for specific uses.

Example 5

Detection of Recombinant Human Factor VIIa (rFVIIa) Activation of Factor FIX on Activated Platelets Using EQELS Spectra 1. Summary FIX can be activated by FXIa or by FVIIa/TF in the presence of calcium. The role of FVIIa/TF in the activation of FIX appears to be the initiating event, although activation of FIX by both mechanisms is important. In the presence of calcium, both FIX and FIXa bind to the activated platelet surface with a Kd of 8 nM and 2 nM, respectively. In the presence of 3 nM rFVIIIa, the binding of FIX and FIXa to activated platelets is tighter with a Kd of 5.8 nM and 0.6 nM, respectively. At rFVIIa concentrations less than 100 nM, no direct binding to the activated platelet surface can be detected with light scattering even in the presence of calcium. However, in the presence of FIX, rFVIIa binds to platelets at concentrations as low as 10 nM rFVIIa. Furthermore, FVIIa on the surface of activated platelets can activate FIX in the absence of tissue factor. This is reflected by an increase binding affinity and a decrease in the FIX Kd from 8 to 1.6 nM. When rFVIIa is added to activated platelets in the presence of both FIX and FVIIIa, the Kd for FIX decreases to 0.6, suggesting that rFVIIa activates FIX on the surface of activated platelets in the absence of tissue factor. The activation of factor IX by FVIIIa on activated platelets can also be demonstrated by a functional assay for FIXa. These data suggest that the effectiveness of pharmacologic doses of rFVIIa in bleeding patients, such as those sustaining severe blunt trauma may be, at least in part, due to the direct activation of FIX by rFVIIa to form additional tenase complexes ultimately resulting in improved thrombin generation. These reactions can occur even in the absence of tissue factor.

2. Introduction

The modem view of the initiation and assembly of coagulation activation complexes such as the tenase complex suggests that cellular surfaces are of fundamental importance for the formation and localization of thrombin generation on the platelet surface resulting in a hemostatic plug. See Monroe, D. M. and Roberts, H. R. *Mechanism of action of high-dose factor VIIa: points of agreement and disagreement. Arterioscler Thromb Vasc. Biol.* (2003) 23(1):8-9. Coagulation initiation involves cell-bound tissue factor (TF) and activated coagulation factor FVII (FVIIa). See Rauch, U., Bonderman, D., Bohrmann, B., Badimon, J. J., Himber, J., Riederer, M. A. and Nemerson Y. *Transfer of tissue factor from leukocytes to platelets is mediated by CD15 and tissue factor. Blood* (2000) 96:170-5. The occupancy of the TF receptor by FVIIa may be important because the TF/FVIIa complex can activate both zymogen factor X (FX) for participation in the prothrombinase complex and zymogen factor IX (FIX) for participation in the tenase complex. In the case of either congenital or acquired deficiencies or inhibition of components of the tenase or prothrombinase complex, either replacement of the missing factor or the use of agents thought to "by-pass" certain deficiencies may restore normal hemostasis. There is now increasing evidence that the administration of pharmacologic doses of recombinant human FVIIa (rFVIIa) may act as a by-passing agent. Evidence to date suggests that the "by-passing" action of rFVIIa is due to both the enhancement of the TF-pathway as well as the direct activation FX by rFVIIa on the surface of activated platelets. See Roberts and Monroe, D. M. *Newer concepts of blood coagulation. Haemophilia.* (1998) 4(4):331-4.

FIX activation may proceed through interaction with TF/FVIIa complex as well as by FXIa, the latter occurring on the surface of activated platelets. Di Scipio, R., Kurachi, K., and Davie, E. W. (1978) *J Clin invest* 61, 1528-1538. Fujikawa, K., Legaz, M., Kato, H., and Davie, E. *The mechanism of activation of bovine factor IX (Christmas factor) by bovine factor XIa, activated plasma thromboplastin antecedent.* (1974) *Biochemistry* 13, 4508-4516; Osterud, B., Bouma, B., and Griffin, J. *Human blood coagulation factor IX. Purification, properties, and mechanism of activation by activated factor XI* (1978) *J Biol Chem* 253, 5946-5951; Kurachi, K., and Davie, E. W. *Isolation and characterization of a cDNA coding for human factor IX* (1982) *Proc Natl Acad Sci USA* 79, 6461-6464; Zur, M., and Nemerson, Y. *Kinetics of factor IX activation via the extrinsic pathway. Dependence of Km on tissue factor* (1980) *J Biol Chem* 255, 5703-5707; Osterud, B., and Rapaport, S. *Activation of factor IX by the reaction product of tissue factor and factor VII: additional pathway for initiating blood coagulation* (1977) *Proc Natl Acad Sci USA* 74, 5260-5264; Hoffman, M., Monroe, D., and Roberts, H. *Coagulation factor IXa binding to activated platelets and platelet-derived microparticles: a flow cytometric study* (1992) *Thromb. Haemost.* 68, 74-78; Hoffman, M., Pratt, C. N. Corbin, L. W., Church, F. C. *Characteristics of the chemotactic activity of heparin cofactor II proteolysis products* (1990) *J. Leukoc. Biol.* 265, 156-162; Bauer, K., Kass, B., ten Case, H., Hawinger, J., and Rosenberg, R. *Factor IX is activated in vivo by the tissue factor mechanism* (1990) *Blood* 76, 731-736. FIXa binds to the activated platelet surface with a Kd of 2.5 nM, but in the presence of rFVIIIa, FIXa binding is tighter with a Kd of 0.6 nM. See Osterud, B., Bouma, B., and Griffin, J. *Human blood coagulation factor IX. Purification, properties, and mechanism of activation by activated factor XI* (1978) *J Biol Chem* 253, 5946-5951; Ahmad, S., Rawala-Sheikh, R., and Walsh, P. *Comparative interactions of factor IX and factor IXa with human platelets J Biol Chem.* 1989 Feb. 25; 264(6):3244-51; Ahmad, S., Rawala-Sheikh, R., Monroe, D., Roberts, H., and Walsh, P. *Comparative platelet binding and kinetic studies with normal and variant factor IXa molecules* (1990) *J Biol Chem* 265, 20907-20911; Ahmad, S., Rawala-Sheikh, R., Cheug, W., Stafford, D., and Walsh, P. *The role of the first growth factor domain of human factor IXa in binding to platelets and in factor X activation* (1992) *J Biol Chem* 267, 8571-8576; Rawala-Sheikh, R., Ahmad, S. S., Ashby, B., Walsh, P. N. *Kinetics of coagulation factor X activation by platelet-bound factor IXa* (1990) *Biochem.* 29, 2606-2611; Rao, L. V., Rapaport, S. I. *Activation of factor VII bound to tissue factor: a key early step in the tissue factor pathway of blood coagulation.* (1988) *Proc. Natl. Acad. Sci.* (USA) 85, 6687-6691. There are approximately 300 binding sites for FIX and 550 for FIXa.

It is widely accepted that complex formation between FVIIa and TF is an obligatory step for the expression of FVIIa activity. See Fujikawa, K., Legaz, M., Kato, H., and Davie, E. *The mechanism of activation of bovine factor IX (Christmas factor) by bovine factor XIa, activated plasma thromboplastin antecedent* (1974) *Biochemistry* 13, 4508-4516; Rao, L. V., Rapaport, S. I. *Activation of factor VII bound to tissue factor: a key early step in the tissue factor pathway of blood coagulation* (1988) *Proc. Natl. Acad. Sci.* (USA) 85, 6687-6691; Nemerson, Y., Gentry, R. *An ordered addition, essential activation model of the tissue factor pathway of coagulation: evidence for a conformational cage* (1986) *Biochem. J* 25, 4020-4033; Lawson, J. H., Mann, K. G. *Cooperative activation of human factor IX by the human extrinsic pathway of blood coagulation* (1991) *J. Biol. Chem.* 266, 11317-11327. However, several studies have demonstrated the TF independent activation of FX by high doses of FVIIa in the presence of calcium ion alone or calcium and phospholipid vesicles. See Born, V., and Bertina, R. *The contributions of $Ca2+$, phospholipids and tissue-factor apoprotein to the activation of human blood-coagulation factor X by activated factor VII* (1990) *Biochem. J.* 265, 327-336; Komiyama, Y., Pederson, A. H., Kisiel, W. *Proteolytic activation of human factors IX and X by recombinant human factor VIIa: effects of calcium, phospholipids, and tissue factor* (1990) *Biochem. J.* 29, 9418-9425; Miletich, J. P., Jackson, C. M., Majerus, P. W. *Interaction of coagulation factor Xa with human platelets* (1977) *Proc. Natl. Acad. Sci.* (USA) 74, 4033-4036; Hoffman, M., Monroe, D. M., Oliver, J. A., and Roberts, H. R. *Factors IXa and Xa play distinct roles in tissue factor-dependent initiation of coagulation* (1995) *Blood* 86, 1794-1801.

By monitoring changes in the binding constant of FIX during its activation by rFVIIa, it can be shown that factor FIX can be converted to FIXa. Unactivated FIX that is bound to activated platelets can provide an interaction site for rFVIIa and the rFVIIa-FIX interaction can lead to activation of FIX. Once FVIIa binds to and activates FIX, the newly formed FIXa in the presence of FVIIIa can be assembled into additional tenase complexes, thus, enhancing thrombin production.

3. Experimental Procedures

Platelet Isolation.

Fresh gel-filtered platelets were used in all experiments. Blood from healthy donors was collected in acid-citrate-dextrose and prostacyclin (5 µg/mL, $PGI_2$, Sigma Chemical Co., St. Louis, Mo.). Platelet-rich-plasma was obtained by centrifugation of the anticoagulated blood at 150 g for 15 minutes. The platelets were isolated from PRP by centrifugation at 650 g for 20 minutes, and resuspended in citrated saline (13 mM citrate, 123 mM NaCl, 50 mM dextrose) buffer containing 5 µg/mL $PGI_2$, washed twice and then resuspended in a small amount of calcium-free albumin-free Tyrode's buffer containing 5 µg/mL prostacyclin ($PGI_2$). Gel-filtered platelets were obtained from the application of washed platelets to a Sepharose CL-2B column (Pharamica Inc., Uppsala, Sweden) equilibrated with calcium-free albumin-free Tyrode's buffer. Platelets for light scattering experiments were suspended in buffer containing 20 mM NaCl, 265 mM sucrose, 2 mM HEPES, pH 7.4 and activated with human α-thrombin (0.2 NIH units/mL). See Li, X., Gabriel, D. A. *The physical exchange of factor VIII (FVIII) between von Willebrand factor and activated platelets and the effect of the FVIII B-domain on platelet binding* (1997) *Biochem. J.* 36, 10760-10767. Fresh gel filtered platelets were shown to activate and aggregate normally with 1 U/ml of human thrombin and 10

μM ADP. EQELS spectra of the gel filtered platelets gave a single homogeneous mobility indicating the lack of microparticles. No change is observed in the platelet mobility spectrum on the addition of rFVIIa over the concentration range where rFVIIa would be expected to bind to tissue factor if it was present, indicating an absence of TF in the preparation.

Proteins.

Blood coagulation FIX and FIXa were purified. See McCord, D. M., Monroe, D. M., Smith, K. J., Roberts, H. R. *Characterization of the functional defect in factor IX Alabama. Evidence for a conformational change due to high affinity calcium binding in the first epidermal growth factor domain.* (1990) *J. Biol. Chem.* 265, 10254-10259. Recombinant human FVIIa (rFVIIa) was provided by Dr. Ulla Hedner of Novo Nordisk, Copenhagen, Denmark. Recombinant human Factor VIII (rFVIII) was provided by Bayer Laboratories Inc., Clayton, N.C.

Electrophoretic Quasi-Elastic Light Scattering (EQELS).

Electrophoretic quasi-elastic light scattering offers the ability to monitor changes in the surface of blood cells resulting from cell activation and ligand binding. Gabriel, D. A., Reece, N., Witte, J., and Muga, K. *Electrophoretic light scattering studies on the interaction of fibrinogen with resting and activated human platelets* (1993) *Blood Coagul. Fibrinolysis* 4, 397-403; Johnson, C., and Gabriel, D. A. (1995) *Laser Light Scattering*, Dover, N.Y. The electrophoretic mobility of activated platelets changes when exposed to a known ligand and that the mobility change is the result of ligand binding. It is the change in the platelet surface charge density and hence its electrophoretic mobility caused by ligand binding and not the ligand itself that is monitored. Under these experimental conditions, resting gel-filtered platelets have an electrophoretic mobility of −0.9 (μ-cm)/(volt-sec) and activated platelets have a mobility of −0.65(μ-cm)/(volt-sec). Loading the platelet surface with a ligand, such as a FIX or FVIII, changes the platelet electrophoretic mobility. While the absolute mobility varies slightly from donor to donor, there is minimal variation in a given donor. The dependence of the change in the platelet electrophoretic mobility on the addition of FIX permits calculation of the binding constant for FIX to the activated platelet. It is not the magnitude of the change in the platelet electrophoretic mobility, μ, that determines the binding constant, but how the change in μ depends on the concentration of the ligand FIX. The effect of ligand binding on the platelet mobility varies with the ligand, and is dependent on the extent of ligand binding, the extent of surface modification caused by ligand binding, and on the net charge of the ligand itself.

EQELS measurements were made on a multi-angle quasi-elastic light scattering spectrometer (DELSA 440, Coulter Electronics, Inc., Hialeah, Fla.). See Li, X., Gabriel, D. A. *Biochem. J.* 36, 10760-10767 (1997); Johnson, C., and Gabriel, D. A. (1995) *Laser Light Scattering*, Dover, N.Y.

Debye Limit.

Charged particles in medium orient oppositely charged counter ions about their surface so that the electrical potential of the particle's surface decreases with the distance from the particle surface. At a distance defined by the Debye-Huckel theory, the particle no longer has an influence on the medium counter ions. The distance from this point to the particle surface is called the Debye-Huckel length, also called the electrical double layer, and for platelets is estimated to be 8 Å. See Jung, S., Kinoshita, K., Tanoue, K., Isohisa, I., and Yamazaki, H. *Role of surface negative charge in platelet function related to the hyperreactive state in estrogen-treated prostatic carcinoma* (1982) *Thromb Haemost* 47, 203-209; Pethica, B. (1961) *Exp Cell Res* 8, 123-140. The electrophoretic mobility for particles the size of blood cells, where the ratio of the particle diameter to the Debye screening length is greater than 30, assuming a platelet diameter of at least 10,000 Å, is governed by the magnitude of the surface charge density and not by frictional factors. See Ware, B. (1974) *Advanced Colloid Interface Science* 4, 1-44. Smoluchawski, M. (1921) *Handbuch der Elektrizitat and des Magnitistons*. (Barth, L., Ed.)

Binding of Proteins to Platelets.

Activated platelets and activated FVIII were prepared by activation with 0.2 NIH U/mL human α-thrombin for 5 minutes. After activation, residual thrombin was inactivated by addition of 2.5 μM phenylalanyl prolinyl arginine chloromethyl ketone (PPACK, Calbiochem, La Jolla, Calif.). FIX, FIXa, FVIIIa, and rFVIIa were incubated with platelets for 10 minutes before EQELS measurements.

The binding coefficient ($K_d$) of the proteins to platelets was determined by fitting the data from the binding experiment to:

$$\mu = \mu_0 + \Delta\mu \frac{[\text{Ligand}]}{K_d + [\text{Ligand}]}$$

where, μ is the electrophoretic mobility, $\mu_0$ is the mobility in the absence of added protein, Δμ is the calculated maximal change in mobility at the saturating concentration of protein. This model assumes one class of binding sites for the specific protein ligand on the platelets. Data was fitted using the nonlinear module (NLIN) of the analysis program SAS (SAS Institute Inc., Cary, N.C.).

Zymogen FIX at varying concentrations was added to the thrombin activated platelets that in some experiments included FVIIIa followed by a 10 minute incubation period. After this incubation period, rFVIIa was added to activated platelets coated with zymogen FIX. The EQELS spectrum was then obtained.

Functional Assays for Activation of FIX and FX.

All assays were run in Tyrodes buffer with 2 mM $CaCl_2$. Platelets were activated with 0.2 NIH units/ml of human α-thrombin for 10 minutes at 37° C. FVIII at 5 units/ml were included with the platelets and thrombin. Thrombin was neutralized with hirudin from a medium titrated against an α-thrombin standard. FVIIa at varying concentrations was added to the platelets for 10 minutes. Plasma concentrations of FIX at 80 nM were added and incubated for varied times. FIXa was assayed in a two stage assay. Platelets with activated FIX were incubated with plasma concentrations of FX for 5 minutes, then the amount of FXa was measured by adding plasma concentrations of prothrombin along with a prothrombin substrate (0.5 mM Perfachrome Th). Pilot studies showed that: FXa generation was linear over the 5 minute assay period, that FXa generation was dependent on FIX, that thrombin generation was dependent on the addition of FX, and that there was no background cleavage of substrate in the absence of prothrombin. Thrombin generation was measured as the change in the absorbance as the p-nitroanilide substrate was cleaved as a function of time. As expected, substrate cleavage fit a second order pattern and the rate of thrombin generation was determined from the first derivative of the absorbance versus time data.

4. Results

Figure 8:
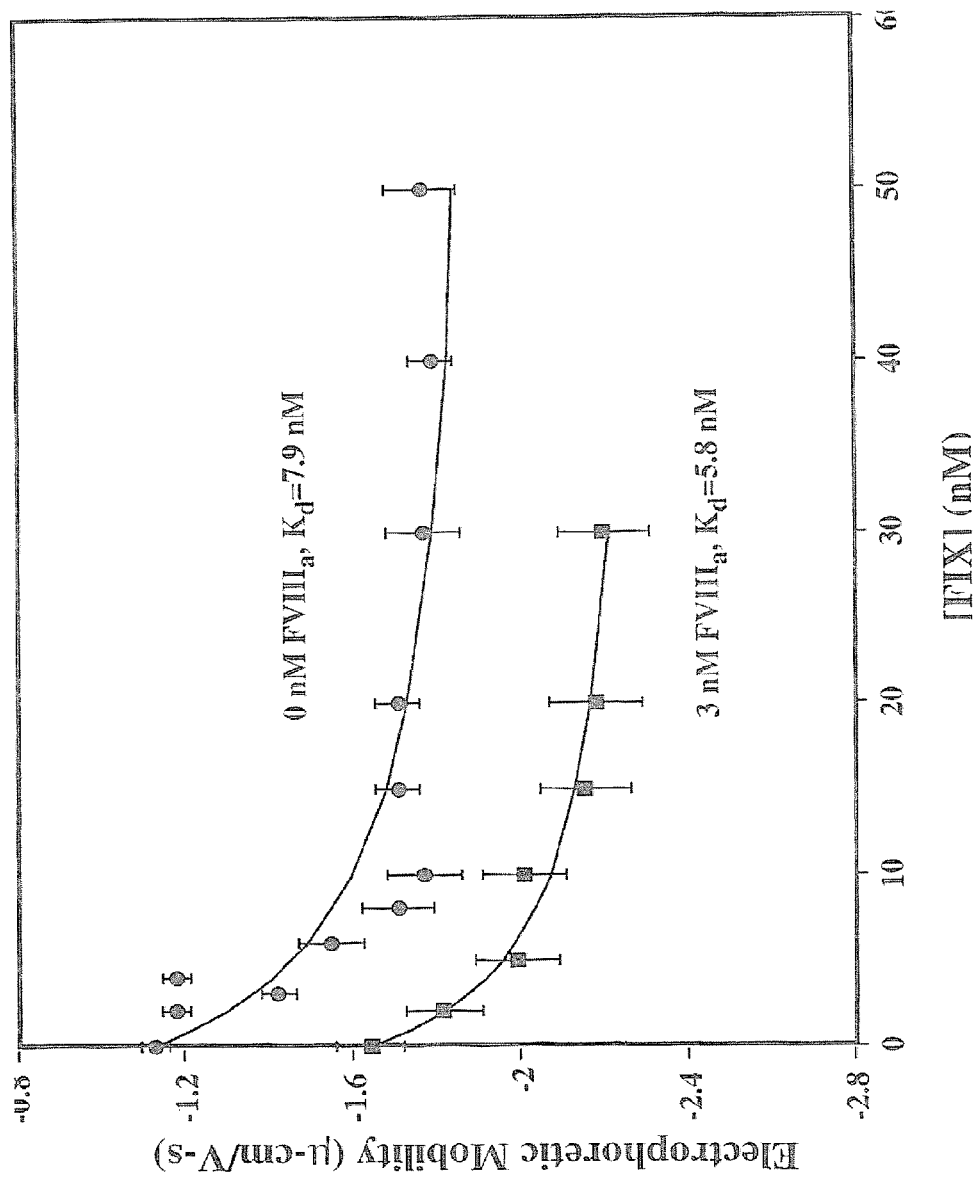
FIG. 8 is a graph illustrating the effect of rFVIIIa on the binding of zymogen FIX to activated platelets in the presence of 4 mM calcium chloride. Platelets are activated with 0.2 NIH U/mL thrombin followed by complete inhibition of thrombin with PPACK. In the absence of rFVIIIa, the binding constant (Kd) for zymogen FIX is 7.9 nM compared to a Kd of 5.8 nM when rFVIIIa is present.

In FIG. 8 the binding profile for zymogen FIX interaction with activated platelets in the presence of 4 mM calcium and in the presence and absence of rFVIIIa is shown. In the absence of rFVIIIa, unactivated FIX binds with a Kd of 7.9 nM (CI=6.948 to 8.851). When 3 nM FVIIIa is present, the binding of FIX to activated platelets is slightly tighter as seen by a decrease in the Kd to 5.8 nM (CI=5.183 to 6.419). These Kd's are different based on comparison of non-overlapping 95% confidence intervals.

Figure 9:
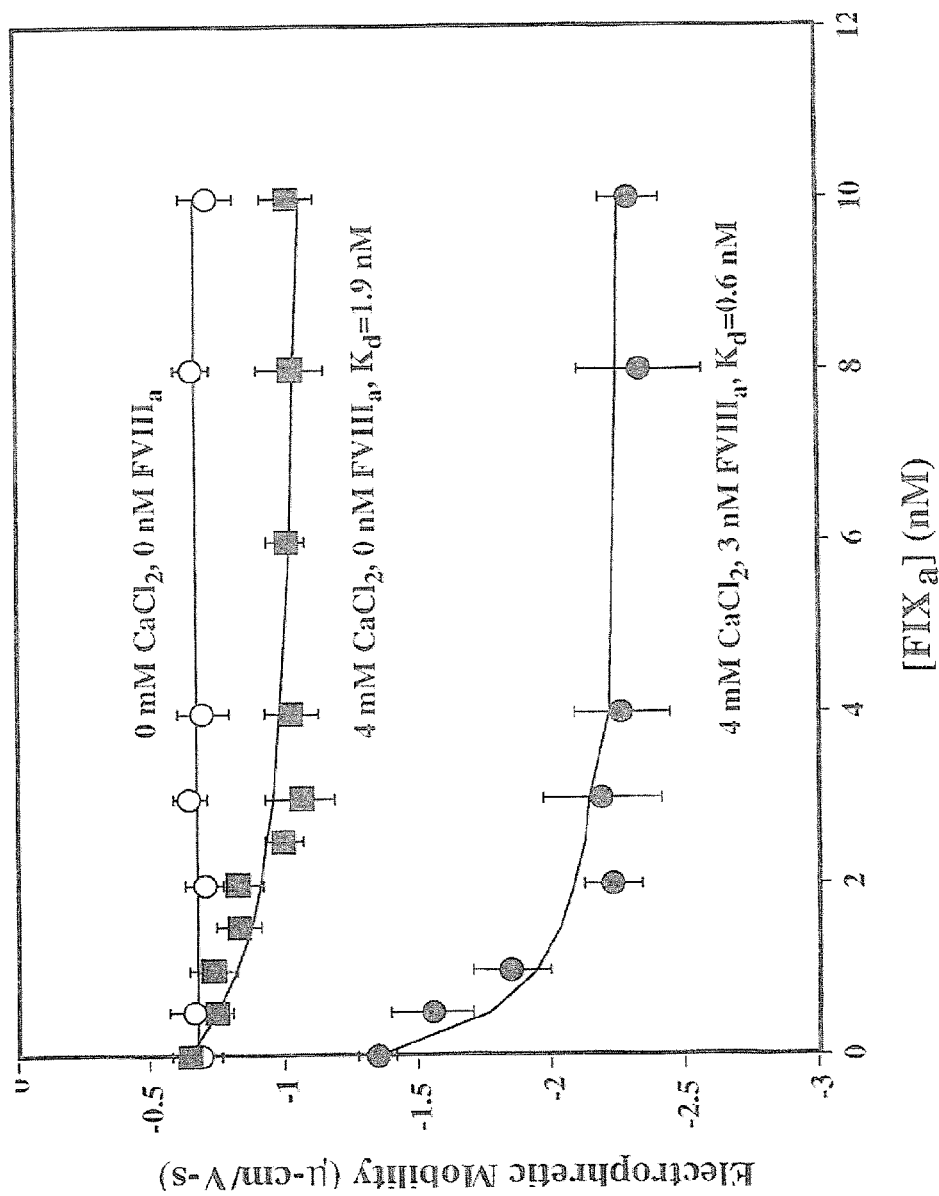
FIG. 9 is a graph illustrating the effect of calcium and rFVIIIa on the binding constant for activated FIX (FIXa). Platelets are activated with 0.2 NIH U/mL thrombin followed by complete inhibition of thrombin with PPACK. In the absence of calcium, no change in the platelet electrophoretic mobility occurs, indicating no binding of FIXa. In the presence of mM calcium chloride, but no rFVIIIa, a binding constant of 1.9 nM is calculated by fitting data to a single state binding model. In the presence of 3 nM (5 U/mL) rFVIIIa and at 0 nM of FIX a, the platelet mobility is increased as a result of rFVIIIa binding. As the concentration of FIXa is increased, the mobility is further increased, which reflects FIX a binding. In the presence of rFVIIIa, a Kd of 0.569 nM is calculated.

FIG. 9 depicts the binding of activated FIX to activated platelets. In contrast to activated platelets, resting platelets do not bind either FIX or FIXa (data not shown). In the presence of 4 mM calcium ion, but no rFVIIIa, FIXa binds to activated platelets with a Kd of 1.9 nM (SE±0.05, CI=1.741 to 2.059). See Roberts and Monroe, D. M. *Newer concepts of blood coagulation Haemophilia.* (1998) 4(4):331-4; Di Scipio, R., Kurachi, K., and Davie, E. W. (1978) *J Clin Invest* 61, 1528-1538; Fujikawa, K., Legaz, M., Kato, H., and Davie, E. *The mechanism of activation of bovine factor IX (Christmas factor) by bovine factor XIa, activated plasma thromboplastin antecedent* (1974) *Biochemistry* 13, 4508-4516; Osterud, B., Bouma, B., and Griffin, J. *Human blood coagulation factor IX. Purification, properties, and mechanism of activation by activated factor XI* (1978) *J Biol Chem* 253, 5946-5951; Kurachi, K., and Davie, E. W. *Isolation and characterization of a cDNA coding for human factor IX* (1982) *Proc Natl Acad Sci USA* 79, 6461-6464; Hoffman, M., Monroe, D., and Roberts, H. *Coagulation factor IXa binding to activated platelets and platelet-derived microparticles: a flow cytometric study* (1992) *Thromb. Haemost.* 68, 74-78; Ahmad, S., Rawala-Sheikh, R., and Walsh, P. *Comparative interactions of factor IX and factor IXa with human platelets J Biol Chem,* 1989 Feb. 5; 264(6):3244-51; Ahmad, S., Rawala-Sheikh, R., Monroe, D., Roberts, H., and Walsh, P. *Comparative platelet binding and kinetic studies with normal and variant factor IXa molecules* (1990) *J Biol Chem* 265, 20907-20911; Rao, L. V., Rapaport, S. L *Activation of factor VII bound to tissue factor: a key early step in the tissue factor pathway of blood coagulation* (1988) *Proc. Natl. Acad. Sci. (USA)* 85, 6687-6691; Lawson, J. H., Mann. K. G. *Cooperative activation of human factor IX by the human extrinsic pathway of blood coagulation* (1991) *J. Biol. Chem.* 266, 11317-11327; Bom, V., and Bertina, R. *The contributions of Ca2+, phospholipids and tissue-factor apoprotein to the activation of human blood-coagulation factor X by activated factor VII* (1990) *Biochem. J.* 265, 327-336. However, as shown in FIG. 9, in the presence of 4 mM calcium and 3 nM rFVIIIa, the Kd for FIXa binding to activated platelets decreases from 1.9 nM to 0.569 nM (SE=0.185, CI=0.188 to 0.950) showing tighter binding. The confidence intervals of the Kd values for FIXa binding with and without rFVIIIa are statistically different at α=0.05. Because of its significant charge, rFVIIIa confers a higher surface charge to the activated platelets, observed by the downward shift of the binding curve when rFVIIIa is present. Li, X., Gabriel, D. A. *Biochem. J.* 36, 10760-10767 (1997).

Because of the difference in the binding constant between FIX and FIXa and since rFVIIa does not bind to activated platelets at 10 nM, the following experiments were performed to investigate the role of rFVIIa in the activation of platelet bound zymogen FIX. A decrease in the Kd of FIX was used to detect activation of zymogen FIX by rFVIIa.

Figure 10:
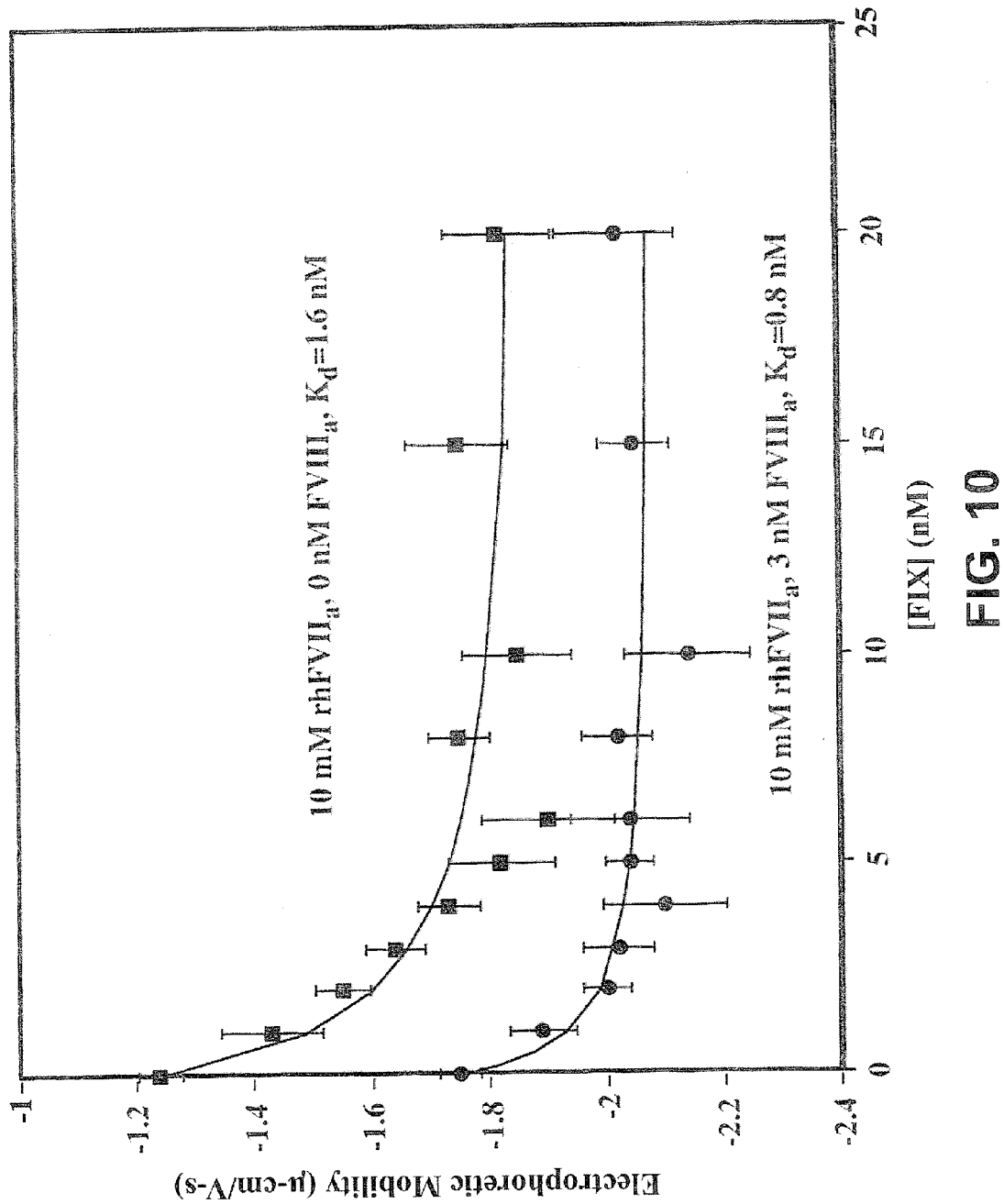
FIG. 10 is a graph illustrating that rFVIIa activates platelet-bound FIX. Platelets are activated with 0.2 NIH U/mL thrombin followed by PPACK inhibition of thrombin. Then rFVIIa at 10 nM, calcium at 4 mM, and 10 nM FIX are added to the activated platelets. The platelet suspension is incubated for 10 minutes and the binding profile for the FIX is determined. If no activation of FIX occurred, the binding curve and the binding coefficient would be similar to that shown in FIG. 8. It was found that the absence of rFVIIIa included in the medium, a binding coefficient for zymogen FIX of 1.62 nM is measured, similar to that shown in FIG. 9 for the binding of FIXa to activated platelets. When 3 nM rFVIIIa is present in the medium, the FIX Kd is 0.84 nM, similar to that for FIXa plus rFVIIIa shown in FIG. 8. Because the binding coefficients similar to these for FIXa binding and not zymogen FIG binding are found, activation by FIX is indicated.

FIG. 10 shows the effect of a high concentration of rFVIIa on the activation of zymogen FIX. In these experiments 10 nM rFVIIa and a variable amount of zymogen FIX (0 to 20 nM) was added to thrombin activated platelets and incubated for 10 minutes followed by the determination of the electrophoretic mobility. When rFVIIa is present at a concentration of 10 nM, FIX binds to activated platelets with a Kd observed for FIXa in the absence of rFVIIIa (Kd=1.62, CI=1.491 to 1.748) compared to a Kd of 1.9 for FIXa shown in FIG. 9. When 3 nM rFVIIIa is first added to the activated platelets, incubated for 10 minutes, followed by addition of zymogen FIX and rFVIIa and reincubated for 10 minutes, the binding is tighter (Kd=0.84, CI=0.287 to 1.393). The difference between these binding curves is also statistically significantly different. The tighter binding is reflected in the decrease in the Kd and is similar to that observed for FIXa binding to platelets in the presence of rFVIIIa (compare to FIG. 9 and Table I). These experiments suggest that at pharmacologic doses of rFVIIa, zymogen FIX is activated by rFVIIa on activated platelets in the absence of TF.

TABLE I

Summary of Binding Coefficients for FIX and FIXa Interaction with Activated Platelets.

| Conditions | FIX | FIXa | FIX + FVIIa* |
|---|---|---|---|
| No Ca$^{++}$, No FVIIIa | — | — | — |
| 4 mM Ca$^{++}$, No FVIIIa | 7.9 (CI 6.95-8.85) | 1.9 (CI 1.74-2.06) | 1.6 (CI 1.49-1.750) |
| 4 mM Ca$^{++}$, 3 nM FVIIIa | 5.8 (CI 5.18-6.42) | 0.57 (CI 0.19-0.95) | 0.84 (CI 0.29-1.39) |

*The Kd for FIX in the presence of FVIIa is very similar to that for direct activation of FIX and indicates that FIX is activated by FVIIa on the activated platelet surface.

Figure 11A:
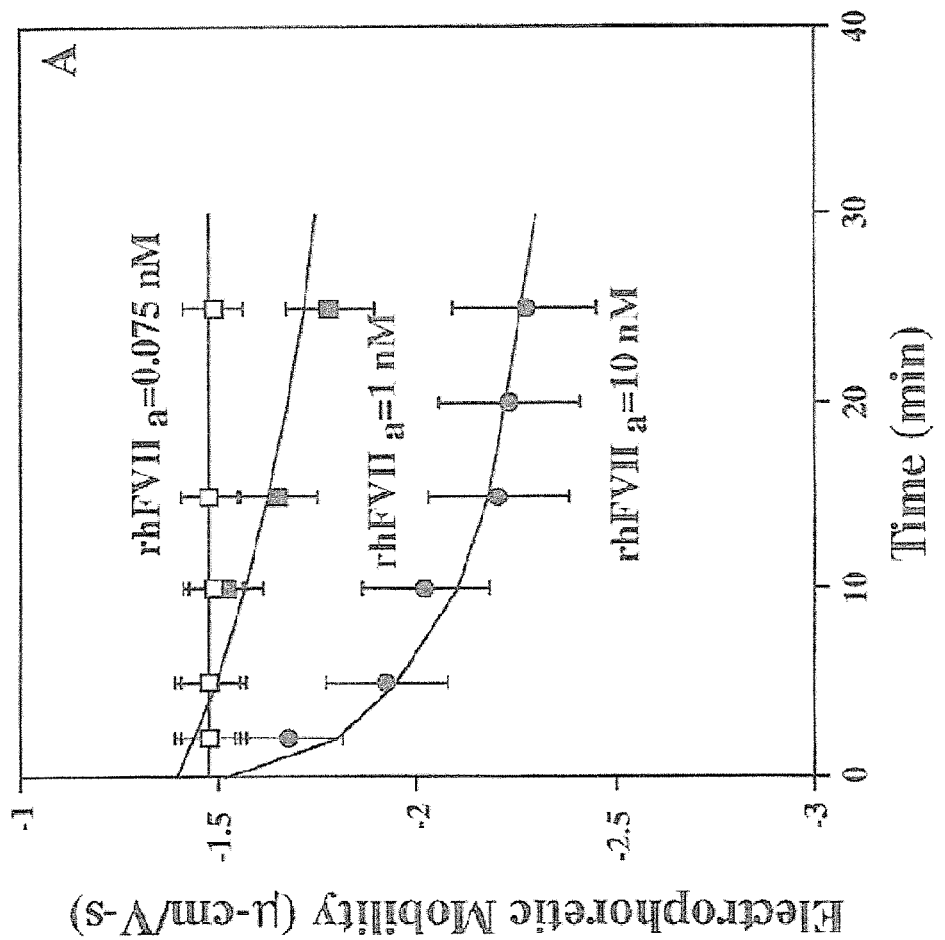
FIG. 11A is a graph of the time and concentration dependence of rFVIIa on the activation of zymogen FIX. Platelets were activated with thrombin followed by inhibition of thrombin with PPACK. The activated platelets were then loaded with rFVIIa (0.075 nM, 1 nM, or 10 nM) and monitored as a function of time. The mobility at the initial time (zero) is the mobility for platelets loaded with zymogen FIX. RFVIIa does not bind to activated platelets in the rFVIIa range of 0.75 to 10 nM. Changes in the platelet mobility result from FIX activation.
Figure 11B:
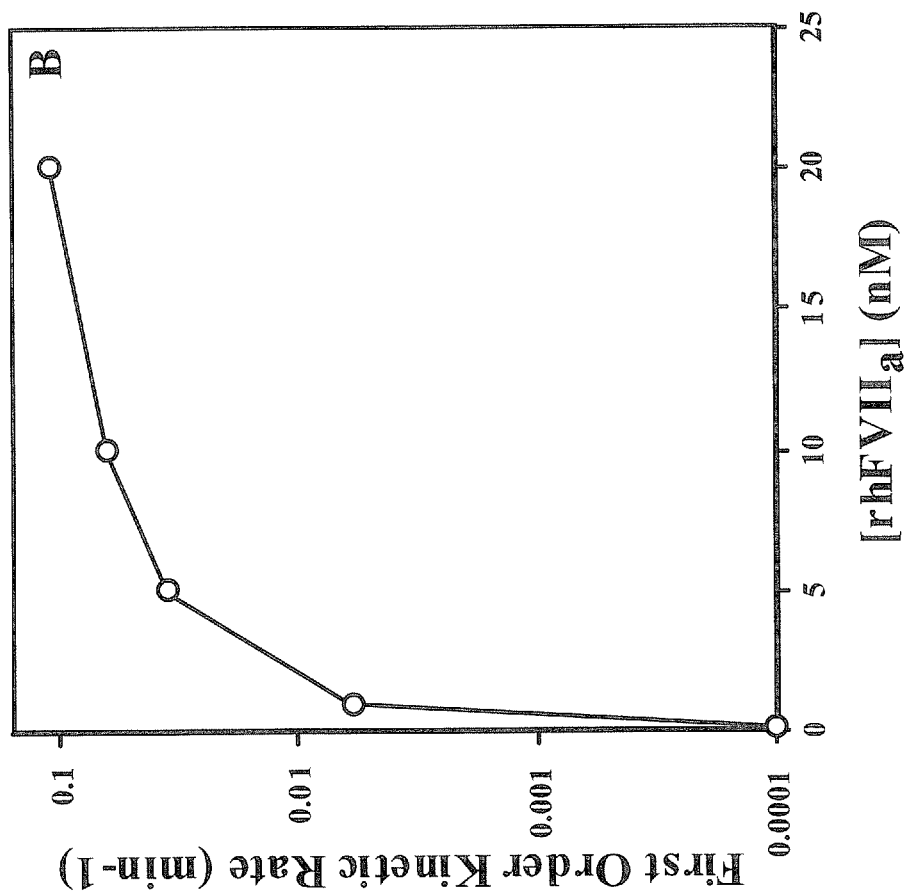
FIG. 11B is a graph illustrating first order rate constants that were calculated for the conversion of zymogen FIX to activated FIXa by rFVIIa. Four concentrations of rFVIIa are shown: 0.75 nM, 1 nM, 10 nM, and 20 nM.

In FIG. 11A the time dependence for the activation of zymogen FIX (10 nM) at different concentrations of rFVIIa is shown. The rate constants for these reactions are shown in FIG. 11B. At 0.075 nM rFVIIa minimal activation of zymogen FIX is observed at approximately 30 minutes (FIG. 11A and the first data point in FIG. 11B). When the concentration of rFVIIa is increased to 1 nM, further activation of zymogen FIX is detected. When the concentration of rFVIIa is further increased to 10 nM, the conversion of zymogen FIX to activated FIX occurs at a still more rapid rate.

Tissue factor was not present on the surface of activated platelets in the experiments presented. The evidence for this is that addition of rFVIIa over a concentration range of 0 to 40 nM did not change the electrophoretic mobility of platelets. If tissue factor were present, rFVIIa would bind to tissue factor and induce an alteration in the platelet surface charge that would be observed as a change in the platelet mobility.

Figure 12:
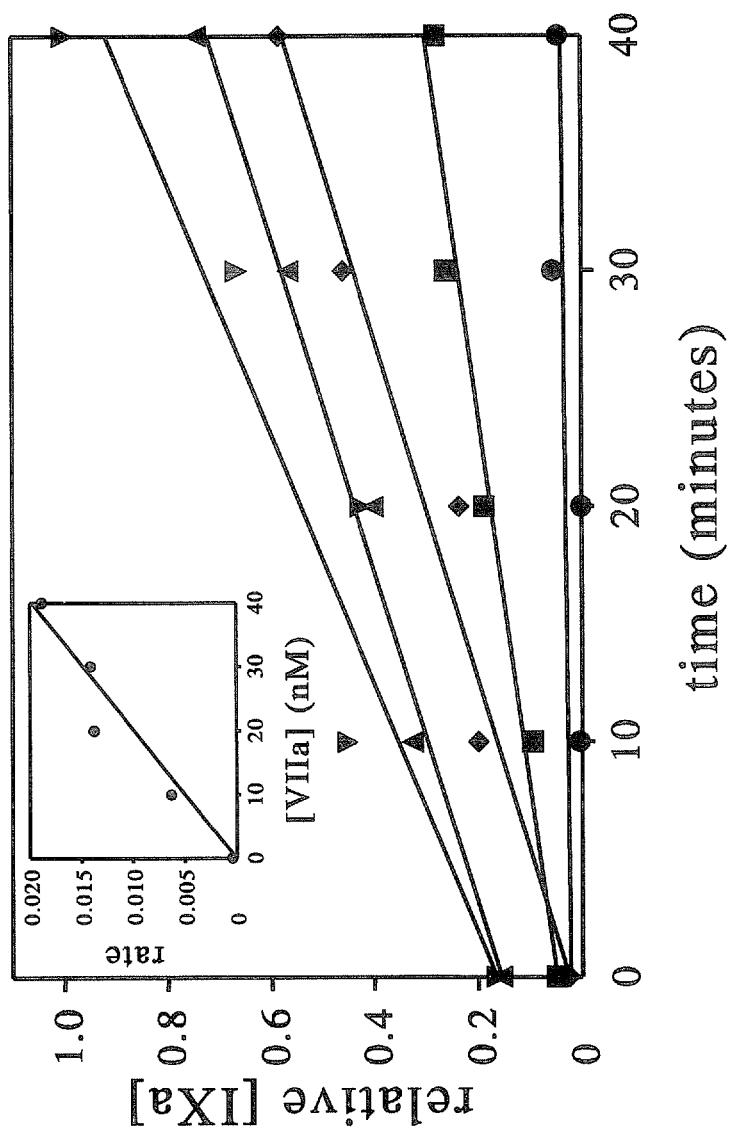
FIG. 12 is a graph illustrating the amount of FIX activated as a function of time and at different concentrations of rFVIIa (between 0 nM and 49 nM) for a chromogenic assay to show activation of FIX by rFVIIa in the absence of TF. The inset of the graph shows the rate constant for FIX activation that corresponds to a specific concentration of rFVIIa.

FIG. 12 provides additional functional evidence for the activation of platelet-bound zymogen FIX by rFVIIa. In the absence of rFVIIa zymogen FIX is not activated (filled circles FIG. 12). As rFVIIa is added at 10 nM (squares), 20 nM (diamonds), 30 nM (inverted triangles), and 40 nM (triangles), the activation of zymogen FIX is shown to be linear in time and directly proportional to the concentration of added rFVIIa. The rate constant for FIX activation as a function of the concentration of added rFVIIa is shown in the inset of FIG. 12. Although not reflected in FIG. 12, it has also been shown that FXa and thrombin are produced in this system and also dependent on the concentration of added rFVIIa. Data shown in FIG. 12 confirms the EQELS result that platelet-bound FIX is activated by rFVIIa.

5. Discussion

A complete understanding of hemostasis, including contributions from platelets, soluble phase coagulation factors, surface effects and fluid dynamics, have been hindered by the complexity of the system. A recent theory for coagulation proposed by Nemerson and others supports TF as the initiating event in hemostasis. See Rauch, U., Bonderman, D., Bohrmann, B., Badimon, J. J., Himber, J., Riederer, M. A. and Nemerson Y. *Transfer of tissue factor from leukocytes to platelets is mediated by CD15 and tissue factor Blood* (2000) 96:170-5; Nemerson, Y. *Tissue factor and hemostasis* (1988) *Blood* 71, 1-8; Rapaport, S. *The extrinsic pathway inhibitor: a regulator of tissue factor-dependent blood coagulation* (1991) *Thromb Haemost* 66, 6-15; Rao, L. V., and Rapaport, S. *The extrinsic pathway inhibitor: a regulator of tissue factor-dependent blood coagulation* (1990) *Blood* 75, 1069-1073; Broze, G. *The role of tissue factor pathway inhibitor in a revised coagulation cascade* (1992) *Sem Hematol* 29, 159-169. Physical separation of the amplifying tenase and prothrombinase complexes from the TF/FVIIa trigger complex provides a spatial feature for regulation of hemostasis. It seems likely that soluble zymogen FIX is first activated by the TF-FVIIa complex at a site distant to the platelet surface and then translocation of activated FIX to the platelet surface. The activated platelet participates in this sequence through tight binding of coagulation factors to specific binding sites, so that amplification complexes can be sequestered, spatially oriented, and protected from plasma inhibitors.

In the special case where high concentrations of rFVIIa are infused as in the treatment of hemophilic patients or for bleeding episodes in non-hemophiliacs, the circumstances for FIX activation may be different. In this case rFVIIa may be bound to other sites in addition to TF. In this scheme, zymogen FIX bound to the activated platelet surface could provide a binding site for rFVIIa, since rFVIIa at physiologic concentrations does not directly bind to the platelet surface itself. It can be shown that at very high concentrations, rFVIIa will bind to platelets in the absence of calcium with a Kd of 250 nM and in the presence of calcium with a Kd of 123 nM (unpublished data). It is estimated that the concentration of rFVIIa after therapeutic infusion for a bleeding diathesis is approximately 30 nM, borderline for binding directly to the activated platelet surface. Under these conditions rFVIIa may bind directly to zymogen FIX bound to the platelet surface. Monroe and colleagues have previously reported evidence that rFVIIa bound to activated platelets can directly activate FX. See Nelsestuen G L, Stone M, Martinez M B, Harvey S B, Foster D, Kisiel W. *Elevated function of blood clotting factor VIIa mutants that have enhanced affinity for membranes: Behavior in a diffusion-limited reaction J Biol Chem.* 2001 Oct. 26; 276(43):39825-31.

Platelets are intimately involved at several steps of the coagulation pathway. It was found that activated platelets promote the activation of FX to form FXa by a complex of FIXa, FVIIIa, and calcium. Ahmad, S., Rawala-Sheikh, R., and Walsh, P. *Platelet receptor occupancy with factor IXa promotes factor X activation* (1989) *J Biol Chem* 264, 20012-20016; Hultin, M. Role of human factor VIII in factor X activation (1982) *J Clin Invest* 69, 950-958; van Rijn, J., Rosing, J., and van Dieijen, G. *Activity of human blood platelets in prothrombin and in factor X activation induced by ionophore A23187.* (1983) *Eur. J. Biochem.* 133, 1-10; Neuenschawander, P., and Jesty, J. *A comparison of phospholipid and platelets in the activation of human factor VIII by thrombin and factor Xa, and in the activation of factor X* (1988) *Blood* 72, 171-177. Activated platelets not only provide the phospholipid surface, but also presumably possess specific, high affinity, saturable binding sites for FXa (See Miletich, J. P., Majerus, D. W. and Majerus, P. W. *A comparison of phospholipid and platelets in the activation of human factor VIII by thrombin and factor Xa, and in the activation of factor X* (1978) *J. Clin. Invest.* 62, 824-831; Tracy, P., Nesheim, M., and Mann, K. *Coordinate binding of factor Va and factor Xa to the unstimulated platelet J Biol. Chem.* 1981 Jan. 25; 256(2):743-51.), FVa (See Tracy, P., Nesheim, M., and Mann, K. *Coordinate binding of factor Va and factor Xa to the unstimulated platelet J Biol. Chem.* 1981 Jan. 25; 256(2):743-51; Tracy, P., Peterson, J., Weisheim, M., McDuffie, F. and Mann, K. *Interaction of coagulation factor V and factor Va with platelet.* (1979) *J. Biol. Chem.* 254, 10354-10361), FVIIIa (See Li, X., Gabriel, D. A. Biochem. J. 36, 10760-10767 (1997), Nesheim, M., Pittman, D., Way, J., Slonosky, D., Giles, A. and Kaufman, R. *The binding of 35S-labeled recombinant factor VIII to activated and unactivated human platelets* (1988) *J. Biol. Chem.* 263, 16467-16470), and FIXa (See Ahmad, S., Rawala-Sheikh, R., and Walsh, P. *Platelet receptor occupancy with factor IXa promotes factor X activation* (1989) *J Biol Chem* 264, 20012-20016). TF-bearing microparticles possible derived from leukocytes appear to be significant to the thrombus perpetuation, but not in the initiation of the thrombus. See Rauch, U., Bonderman, D., Bohrmann, B., Badimon, J. J., Himber, J., Riederer, M. A. and Nemerson Y. *Transfer of tissue factor from leukocytes to platelets is mediated by CD15 and tissue factor Blood* (2000) 96:170-5. Microparticles containing TF that localize to activated platelets that normally do not contain TF has been shown to be mediated by P-selectin on the platelet surface and CD15 on the microparticle. See Rauch, U., Bonderman, D., Bohrmann, B., Badimon, J. J., Himber, J., Riederer, M. A. and Nemerson Y. *Transfer of tissue factor from leukocytes to platelets is mediated by CD15 and tissue factor Blood* (2000) 96:170-5; Giesen, P. L., Rauch, U., Bohrmann, B., Kling, D., Roque, M, Fallon, J. T Badimon, J. J, Himber, J, Riederer, M. A. and Nemerson, Y. *Blood-borne tissue factor: another view of thrombosis.* Proc Natl Acad Sci USA. (1999) 96:2311-2315; Halvorsen, H., Olsen, J. O. and Osterud, B. *Granulocytes enhance LPS-induced tissue factor activity in monocytes via an interaction with platelets. J Leukoc Biol.* (1993) 54:275-82; Huge, B, Socie, G., Vu, T., Toti, F., Gluckman, E., Freyssinet, J. M. and Scrobohaci, M. L. *Elevated levels of circulating procoagulant microparticles in patients with paroxysmal nocturnal hemoglobinuria and aplastic anemia Blood.* (1999) 93:3451-6; Kirchhofer, D., Riederer, M. A. and Baumgartner, H. R. *Specific accumulation of circulating monocytes and polymorphonuclear leukocytes on platelet thrombi in a vascular injury model Blood.* (1997) 89:1270-8.

The changes observed in the platelet surface charge as the concentration of FIXa is increased (FIG. 9) are due to binding of FIXa to the platelet surface since: 1) the binding is saturable, 2) the change requires the presence of calcium, 3) platelet activation is required, 4) saturation with other proteins does not inhibit the effect, and 5) a protein highly homologous to Factor IXa, i.e., FVIIa, does not change the platelet surface charge under identical conditions. At concentrations of rFVIIa greater than 100 nM the binding of rFVIIa to activated platelets can be detected. The possible role of TF-containing microparticles as a source for this effect under these conditions is unlikely since a mobility corresponding to microparticles in the mobility spectrum is not observed. Additionally, no change in the platelet mobility occurs when rFVIIa is added at concentrations that should bind TF. Further support for specific FIXa binding is appreciated from the increased affinity of activated platelets for FIX in the presence of rFVIIIa (1.9 nM to 0.569 nM). Ahmad, S., Rawala-Sheikh, R., and Walsh, P. *Platelet receptor occupancy with factor IXa promotes factor X activation* (1989) *J Biol Chem* 264, 20012-20016.

Previous studies on platelet activation monitored by EQELS showed that platelet activation results in a reduction in the surface charge probably due to the exposure of specific binding sites and their occupancy by specific ligands. Li, X., Gabriel, D. A. *Biochem. J.* 36, 10760-10767 (1997). Gabriel, D. A., Reece, N., Witte, J., and Muga, K. *Blood Coagul. Fibrinolysis* 4, 397-403 (1993). The exact mechanism for the platelet surface charge modification during platelet activation is not known. It is known that many surface events occur with platelet activation, e.g., exposure of CD62, FVa, various receptors, appearance of phosphatidyl serine, etc., all of which could contribute to changes in the platelet surface charge. Electrophoretic light scattering can monitor these changes. After platelet activation is complete, the surface charge on the platelet surface stabilizes until a ligand is bound to the activated surface. Electrophoretic light scattering is also highly sensitive in monitoring the ligand-activated platelet surface interaction.

One important result of these experiments is that high concentrations of rFVIIa can activate FIX even in the absence of tissue factor, which may explain its effect in the correction of bleeding in non-hemophiliacs who have a severe hemorrhagic diathesis.

The foregoing embodiments are illustrative of the present invention and are not to be construed as limiting thereof. The invention is defined by the following claims, with equivalents of the claims to be included therein.

That which is claimed is:

1. A method of identifying a biological particle in a sample medium, said method comprising: generating an Electrophoretic Quasi-elastic Light Scattering (EQELS) spectrum for said biological particle in said sample medium; comparing said EQELS spectrum to a reference database comprising a plurality of spectra, each of said plurality of spectra corresponding to an EQELS spectrum for one of a plurality of known biological particles; and identifying said biological particle in said sample medium from said comparison,
wherein the reference database comprises EQELS spectra obtained before the EQELS spectra generated for said biological particle in said sample medium is obtained, and does not comprise EQELS spectra generated after the EQELS spectra generated for said biological particle in said sample medium is obtained.

2. The method of claim 1, wherein said biological particle is a biological cell.

3. A method of identifying a biological particle in a sample medium, said method comprising: generating an Electrophoretic Quasi-elastic Light Scattering (EQELS) spectrum for said biological particle in said sample medium; comparing said EQELS spectrum to a reference database comprising a plurality of spectra, each of said plurality of spectra corresponding to an EQELS spectrum for one of a plurality of known biological particles; and identifying said biological particle in said sample medium from said comparison,
wherein said biological particle is a microbe selected from the group consisting of viruses, bacteria, fungi, and protozoa, and
wherein the reference database comprises EQELS spectra obtained before the EQELS spectra generated for said biological particle in said sample medium is obtained, and does not comprise EQELS spectra generated after the EQELS spectra generated for said biological article in said sample medium is obtained.

4. The method of claim 1, wherein said EQELS spectrum comprises a first EQELS spectrum, said method further comprising: modifying said sample medium; generating a second EQELS spectrum for said biological particle in said sample medium after modifying said sample medium; comparing said first EQELS spectrum to said second EQELS spectrum; and characterizing said biological particle in said sample medium from said comparison.

5. The method of claim 4, wherein said biological particle is a microbe and wherein said step of modifying said sample medium comprises adding an antibody to said sample medium, wherein said antibody is a specific binder to a predetermined microbe; and wherein said step of characterizing said microbe comprises determining if said microbe in said sample medium is said predetermined microbe from said comparison of said first EQELS spectrum to said second EQELS spectrum.

6. The method of claim 4, wherein said step of modifying said sample medium is selected from the group consisting of: (I) adding a binder for a target biological particle to said sample medium; (ii) adding a solvent to said sample medium; (iii) changing a pH of said sample medium; (iv) changing a temperature of said sample medium; (v) changing an ionic strength of said sample medium; (vi) adding an agent for altering binding of a target biological particle to said sample medium; and (vii) adding a complexation agent for a target biological particle to said sample medium.

7. The method of claim 4, wherein said step of modifying said sample medium comprises adding a binder for a target biological particle to said sample medium, wherein said binder is selected from the group consisting of: antibodies, cells, microbes, ligands, proteins, peptides, nucleic acids, polysaccharides, lipids, lipoproteins, haptens, and pharmaceutical compounds.

8. The method of claim 1, wherein said sample medium comprises a fluid selected from the group consisting of: blood, blood products, water, cerebrospinal fluid, ascites, pleural fluid, and synovial fluid.

9. The method of claim 4, wherein said step of characterizing said biological particle comprises determining at least one characteristic of said biological particle, wherein said at least one characteristic is selected from the group consisting of: an electrophoretic mobility, a biological particle concentration, a cytostatic character, a cytotoxic character, a swimming rate, a biological particle volume, a surface charge, a binding strength, a binding constant, a binding profile, a ratio of a swim rate to an electrophoretic mobility, a diffusion constant, a biological particle size, a ratio of a dimension to an electrophoretic mobility, a structure; a gyration ratio, a binding energy, a binding specificity, a binding site mapping, and an enzyme activation on a surface of said biological particle.

10. The method of claim 4, said wherein said step of modifying said sample medium comprises adding a therapeutic agent to said sample medium, and wherein said step of characterizing said biological particle comprises assessing an effectiveness of said therapeutic agent based on said comparison of said first EQELS spectrum and said second EQELS spectrum.

11. The method of claim 10, wherein said step of assessing an effectiveness comprises determining if said therapeutic agent binds to a surface of said biological particle.

12. The method of claim 10, wherein said biological particle is a microbe and wherein said step of assessing an effectiveness comprises determining a change in swim rate of said microbe.

13. The method of claim 10, wherein said step of assessing an effectiveness comprises determining a binding constant for said therapeutic agent.

14. The method of claim 3, wherein said biological particle comprises a microbe, the method further comprising determining a swim rate for said microbe, wherein said reference database includes swim rates for a plurality of known microbes.

15. The method of claim 1, wherein said step of an EQELS spectrum comprises: exposing said biological particle in said sample medium to an electric field; impinging light from a light source on said biological particles in said sample medium to produce scattered light; detecting said scattered light; and detecting a Doppler shift in said scattered light compared to impinged light from said light source.

16. The method of claim 3, further comprising collecting said biological particle using a filtration device.

17. The method of claim 16, wherein said collecting step further comprises: filtering a gas and/or liquid with a filter to trap said biological particle; and flushing said filter with a fluid to provide said sample medium.

18. The method of claim 16, wherein said collecting step is conducted automatically.

19. A method of identifying a biological particle in a sample medium, said method comprising: generating an Electrophoretic Quasi-elastic Light Scattering (EQELS) spectrum for said biological particle in said sample medium; comparing said EQELS spectrum to a reference database comprising a plurality of spectra, each of said plurality of spectra corresponding to an EQELS spectrum for one of a plurality of known biological particles; and identifying said biological particle in said sample medium from said comparison,
wherein the reference database is stored in a memory of a computer processor.

20. The method of claim 19, wherein said biological particle is a biological cell.

21. The method of claim 19, wherein said EQELS spectrum comprises a first EQELS spectrum, said method further comprising: modifying said sample medium; generating a second EQELS spectrum for said biological particle in said sample medium after modifying said sample medium; comparing said first EQELS spectrum to said second EQELS spectrum; and characterizing said biological particle in said sample medium from said comparison.

22. The method of claim 21, wherein said biological particle is a microbe and wherein said step of modifying said sample medium comprises adding an antibody to said sample medium, wherein said antibody is a specific binder to a predetermined microbe; and wherein said step of characterizing said microbe comprises determining if said microbe in said sample medium is said predetermined microbe from said comparison of said first EQELS spectrum to said second EQELS spectrum.

23. The method of claim 21, wherein said step of modifying said sample medium is selected from the group consisting of: (I) adding a binder for a target biological particle to said sample medium; (ii) adding a solvent to said sample medium; (iii) changing a pH of said sample medium; (iv) changing a temperature of said sample medium; (v) changing an ionic strength of said sample medium; (vi) adding an agent for altering binding of a target biological particle to said sample medium; and (vii) adding a complexation agent for a target biological particle to said sample medium.

24. The method of claim 21, wherein said step of modifying said sample medium comprises adding a binder for a target biological particle to said sample medium, wherein said binder is selected from the group consisting of: antibodies, cells, microbes, ligands, proteins, peptides, nucleic acids, polysaccharides, lipids, lipoproteins, haptens, and pharmaceutical compounds.

25. The method of claim 19, wherein said sample medium comprises a fluid selected from the group consisting of: blood, blood products, water, cerebrospinal fluid, ascites, pleural fluid, and synovial fluid.

26. The method of claim 21, wherein said step of characterizing said biological particle comprises determining at least one characteristic of said biological particle, wherein said at least one characteristic is selected from the group consisting of: an electrophoretic mobility, a biological particle concentration, a cytostatic character, a cytotoxic character, a swimming rate, a biological particle volume, a surface charge, a binding strength, a binding constant, a binding profile, a ratio of a swim rate to an electrophoretic mobility, a diffusion constant, a biological particle size, a ratio of a dimension to an electrophoretic mobility, a structure; a gyration ratio, a binding energy, a binding specificity, a binding site mapping, and an enzyme activation on a surface of said biological particle.

27. The method of claim 21, said wherein said step of modifying said sample medium comprises adding a therapeutic agent to said sample medium, and wherein said step of characterizing said biological particle comprises assessing an effectiveness of said therapeutic agent based on said comparison of said first EQELS spectrum and said second EQELS spectrum.

28. The method of claim 27, wherein said step of assessing an effectiveness comprises determining if said therapeutic agent binds to a surface of said biological particle.

29. The method of claim 27, wherein said biological particle is a microbe and wherein said step of assessing an effectiveness comprises determining a change in swim rate of said microbe.

30. The method of claim 27, wherein said step of assessing an effectiveness comprises determining a binding constant for said therapeutic agent.

31. The method of claim 19, wherein said step of an EQELS spectrum comprises: exposing said biological particle in said sample medium to an electric field; impinging light from a light source on said biological particles in said sample medium to produce scattered light; detecting said scattered light; and detecting a Doppler shift in said scattered light compared to impinged light from said light source.

32. A method of identifying a biological particle in a sample medium, said method comprising: generating an Electrophoretic Quasi-elastic Light Scattering (EQELS) spectrum for said biological particle in said sample medium; comparing said EQELS spectrum to a reference database comprising a plurality of spectra, each of said plurality of spectra corresponding to an EQELS spectrum for one of a plurality of known biological particles; and identifying said biological particle in said sample medium from said comparison,
wherein said biological particle is a microbe selected from the group consisting of viruses, bacteria, fungi, and protozoa, and
wherein the reference database is stored in a memory of a computer processor.

33. The method of claim 32, wherein said biological particle comprises a microbe, the method further comprising determining a swim rate for said microbe, wherein said reference database includes swim rates for a plurality of known microbes.

34. The method of claim 23, further comprising collecting said biological particle using a filtration device.

35. The method of claim 34, wherein said collecting step further comprises: filtering a gas and/or liquid with a filter to trap said biological particle; and flushing said filter with a fluid to provide said sample medium.

36. The method of claim 34, wherein said collecting step is conducted automatically.

* * * * *

UNITED STATES PATENT AND TRADEMARK OFFICE
CERTIFICATE OF CORRECTION

| | | |
|---|---|---|
| PATENT NO. | : 8,551,405 B2 | Page 1 of 1 |
| APPLICATION NO. | : 12/512306 | |
| DATED | : October 8, 2013 | |
| INVENTOR(S) | : Gabriel | |

It is certified that error appears in the above-identified patent and that said Letters Patent is hereby corrected as shown below:

In the Specification:

Column 19, Line 11: Correct "(SE±0.05, CI=1.741 to 2.059)."
to read -- (SE = 0.05, CI =1.741 to 2.059). --

In the Claims:

Column 24, Claim 3, Line 2: Correct "for said biological article"
to read -- for said biological particle --

Signed and Sealed this
Eleventh Day of November, 2014

Michelle K. Lee
*Deputy Director of the United States Patent and Trademark Office*